United States Patent
Imamura et al.

(10) Patent No.: US 10,610,171 B2
(45) Date of Patent: Apr. 7, 2020

(54) RADIOGRAPHY SYSTEM AND METHOD FOR OPERATING RADIOGRAPHY SYSTEM

(71) Applicant: FUJIFILM Corporation, Tokyo (JP)

(72) Inventors: Ryo Imamura, Ashigarakami-gun (JP); Masato Hattori, Ashigarakami-gun (JP); Koichi Kitano, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 44 days.

(21) Appl. No.: 16/059,971

(22) Filed: Aug. 9, 2018

(65) Prior Publication Data

US 2019/0046130 A1 Feb. 14, 2019

(30) Foreign Application Priority Data

Aug. 10, 2017 (JP) .................. 2017-156067

(51) Int. Cl.
| | |
|---|---|
| *A61B 6/08* | (2006.01) |
| *A61B 6/00* | (2006.01) |
| *H04N 5/32* | (2006.01) |
| *H05G 1/60* | (2006.01) |

(52) U.S. Cl.
CPC .............. *A61B 6/08* (2013.01); *A61B 6/4028* (2013.01); *A61B 6/4283* (2013.01); *A61B 6/4405* (2013.01); *A61B 6/464* (2013.01); *A61B 6/465* (2013.01); *A61B 6/466* (2013.01); *A61B 6/467* (2013.01); *A61B 6/505* (2013.01); *A61B 6/5247* (2013.01); *A61B 6/566* (2013.01); *A61B 6/587* (2013.01); *H04N 5/32* (2013.01); *H05G 1/60* (2013.01)

(58) Field of Classification Search
CPC ....... A61B 6/08; A61B 6/4028; A61B 6/4283; A61B 6/4405; A61B 6/464; A61B 6/465; A61B 6/466; A61B 6/467; A61B 6/505; A61B 6/5247; A61B 6/566; A61B 6/587; H04N 5/32; H05G 1/60
USPC .......................................................... 378/62
See application file for complete search history.

(56) References Cited

U.S. PATENT DOCUMENTS

| | | | | | |
|---|---|---|---|---|---|
| 5,539,798 | A | * | 7/1996 | Asahina ................. | A61B 6/022 |
| | | | | | 348/E5.086 |
| 2002/0012450 | A1 | * | 1/2002 | Tsujii ...................... | H04N 5/32 |
| | | | | | 382/103 |
| 2010/0054416 | A1 | * | 3/2010 | Tsubota .................. | A61B 6/00 |
| | | | | | 378/98 |

(Continued)

FOREIGN PATENT DOCUMENTS

| | | |
|---|---|---|
| JP | 6-217973 A | 8/1994 |
| JP | 2013-48740 A | 3/2013 |

*Primary Examiner* — Taeho Jo
(74) *Attorney, Agent, or Firm* — Birch, Stewart, Kolasch & Birch, LLP

(57) ABSTRACT

A composite image generation unit of a CPU of a console combines a camera image obtained by capturing an image of a subject located in an irradiation field using a camera and a positioning index image indicating a set position of the subject, which has been set in advance with respect to an in-image cassette position that is the position of the electronic cassette in the camera image, to generate a composite image. In a case in which the in-image cassette position is changed with the movement of the electronic cassette, the composite image generation unit changes a display position of the positioning index image with the change in the in-image cassette position.

20 Claims, 33 Drawing Sheets

(56) References Cited

U.S. PATENT DOCUMENTS

| | | | |
|---|---|---|---|
| 2010/0079273 A1* | 4/2010 | Tsubota | H04W 48/02 340/539.1 |
| 2010/0140492 A1* | 6/2010 | Tsubota | G03B 42/04 250/393 |
| 2010/0148085 A1* | 6/2010 | Yoshida | G01T 1/00 250/395 |
| 2010/0243910 A1* | 9/2010 | Tsubota | A61B 6/4283 250/393 |
| 2012/0250825 A1* | 10/2012 | Yoshida | A61B 6/4233 378/91 |
| 2013/0121468 A1* | 5/2013 | Ohta | A61B 6/4405 378/63 |
| 2013/0259196 A1* | 10/2013 | Tajima | A61B 6/42 378/62 |
| 2014/0056409 A1* | 2/2014 | Nishino | G06T 1/0007 378/62 |
| 2014/0275954 A1* | 9/2014 | Ohta | G16H 40/63 600/407 |
| 2015/0222134 A1* | 8/2015 | Ikegame | H02J 7/0045 320/107 |
| 2015/0279196 A1* | 10/2015 | Tajima | G08B 13/22 340/539.32 |
| 2016/0015340 A1* | 1/2016 | Nenoki | A61B 6/4283 378/98 |
| 2016/0081650 A1* | 3/2016 | Okusu | A61B 6/56 378/62 |
| 2016/0174918 A1* | 6/2016 | Wang | A61B 6/4405 378/63 |
| 2017/0135667 A1* | 5/2017 | Becker | A61B 6/4411 |
| 2017/0219498 A1* | 8/2017 | Chtcheprov | G01N 23/046 |

* cited by examiner

| IMAGE ID | IF0001 |
|---|---|
| IMAGING DATE AND TIME | 7/10/2017 11:05 |
| SUBJECT ID | H0500 |
| NAME | ○○○○ |
| SEX | MALE |
| DATE OF BIRTH | 09/25/1985 |
| AGE | 28 |
| HEIGHT | 183 |
| WEIGHT | 78 |
| ORDER ID | OD0001 |
| IMAGING MENU | KNEE/ FLEXED POSITION/ SIDE |
| TUBE VOLTAGE | 100 |
| TUBE CURRENT | 200 |
| IRRADIATION TIME | 20 |

FIG. 10

| IMAGING MENU | POSITIONING INDEX IMAGE |
|---|---|
| CHEST/ DECUBITUS POSITION/ FRONT | II 0001 |
| CHEST/ DECUBITUS POSITION/ REAR | II 0002 |
| KNEE/ FLEXED POSITION/ SIDE | II 0020 |

FIG. 12
(A)
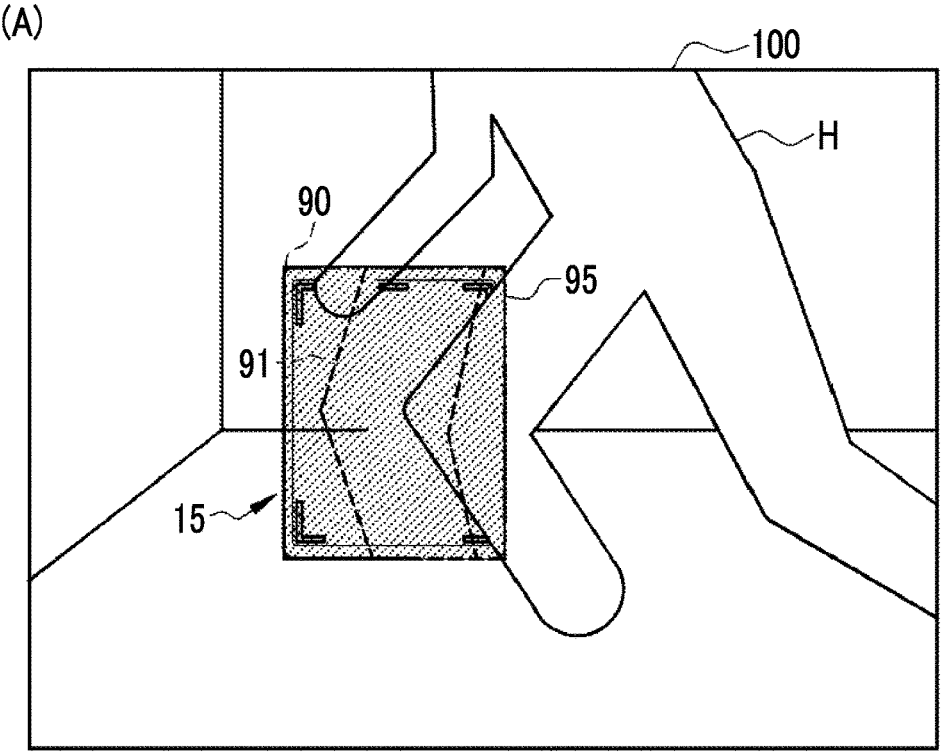
(B)
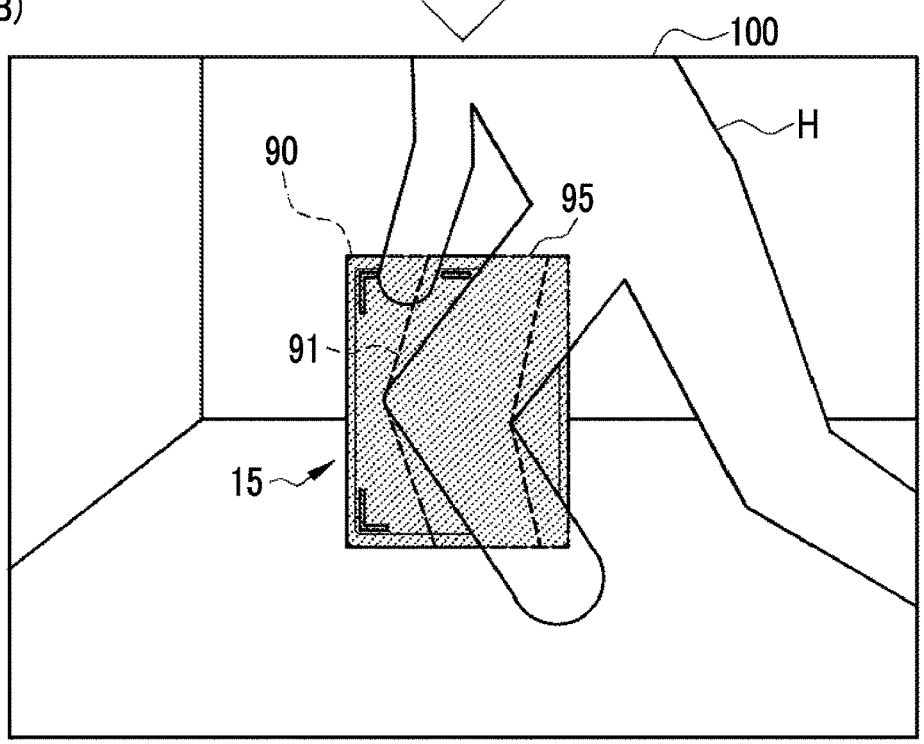

FIG. 14

| IMAGING MENU | POSITIONING INDEX IMAGE |
|---|---|
| CHEST/ DECUBITUS POSITION/ FRONT | ![] 106, II 0100, 107 |
| CHEST/ DECUBITUS POSITION/ REAR | ![] II 0101, 106 |
| KNEE/ FLEXED POSITION/ SIDE | ![] 107, II 0120, 106 |
| KNEE/ SEATED POSITION/ SIDE | ![] 107, II 0121, 106 |

105

FIG. 16
(A)
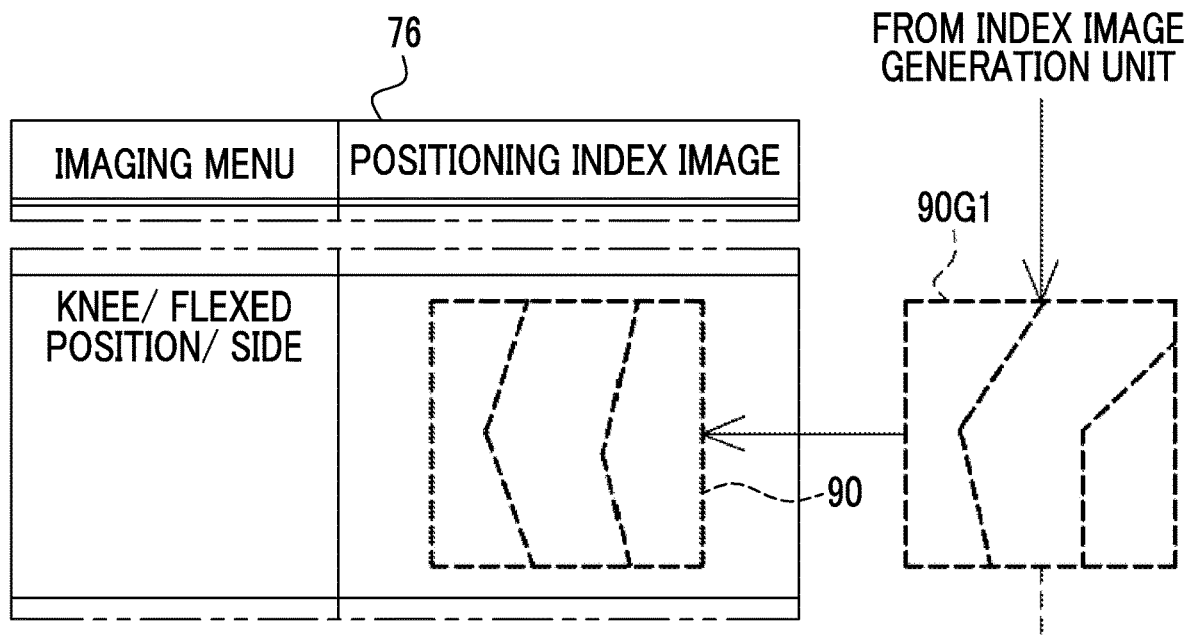
(B)
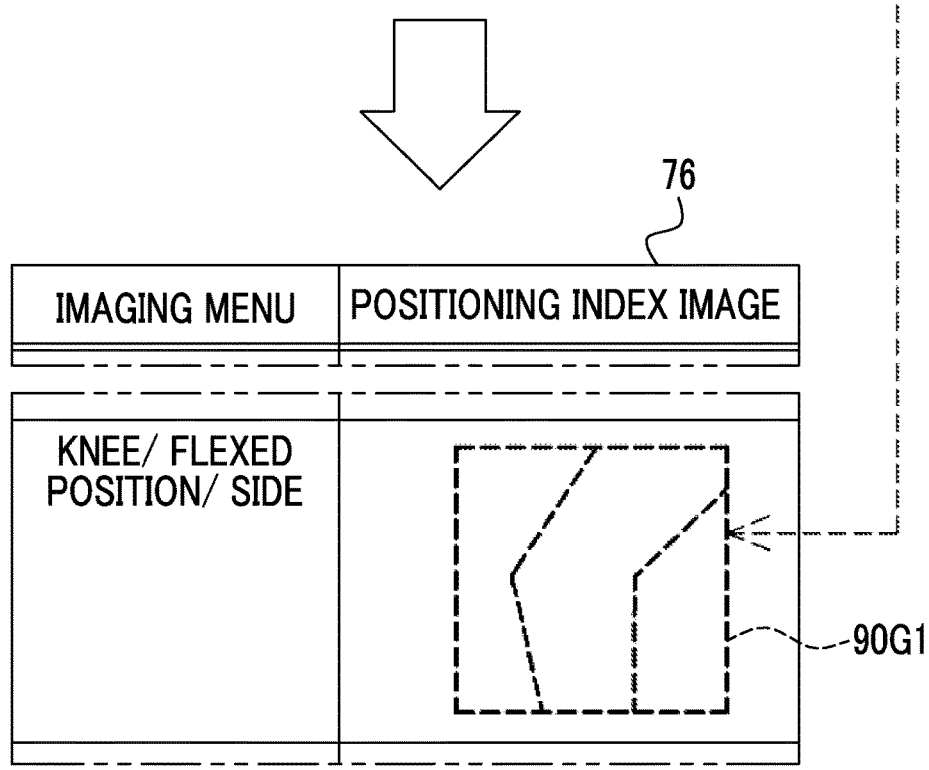

FIG. 20
(A)
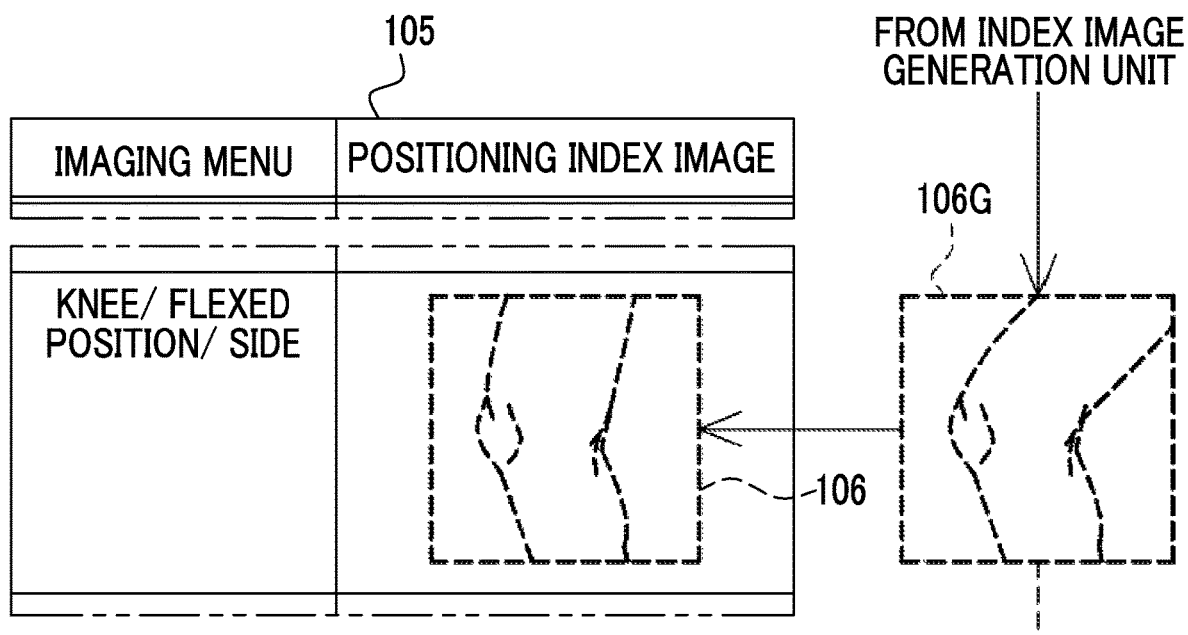
(B)
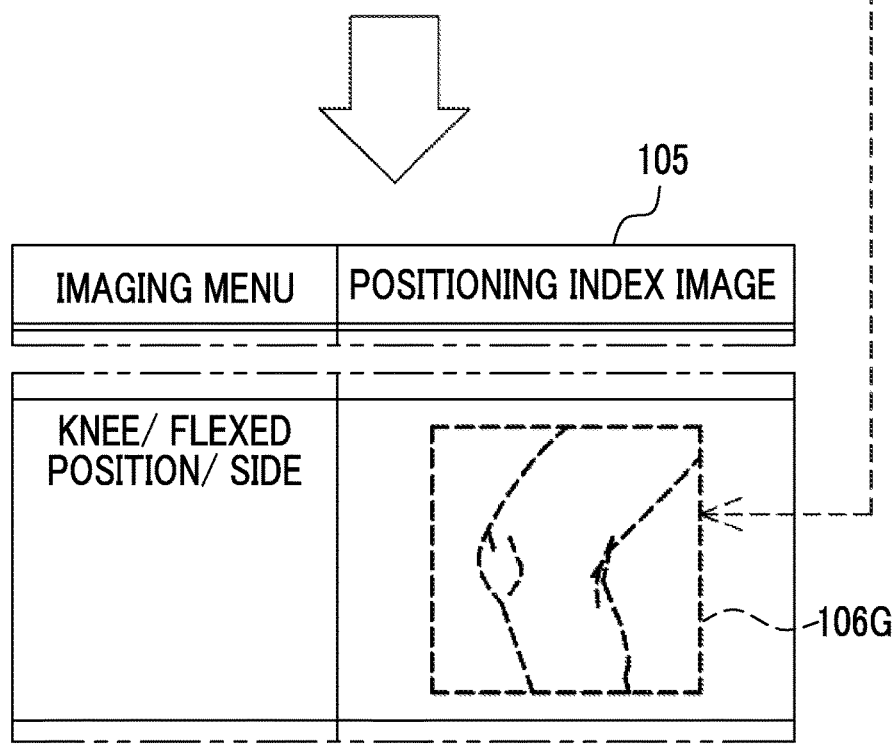

FIG. 21

| SUBJECT ID | IMAGING MENU | POSITIONING INDEX IMAGE |
|---|---|---|
| H0100 | CHEST/ DECUBITUS POSITION/ FRONT | II 0001 — 90 |
|  | CHEST/ DECUBITUS POSITION/ REAR | II 0002 — 90 |
| H0500 | KNEE/ FLEXED POSITION/ SIDE | II 0020 — 90 |
| H0800 | KNEE/ FLEXED POSITION/ SIDE | II 0025 — 90 |

| IMAGING MENU | BODY TYPE | POSITIONING INDEX IMAGE |
|---|---|---|
| CHEST/ DECUBITUS POSITION/ FRONT | THIN BODY TYPE | II 0001-S   90S, 91 |
| | NORMAL BODY TYPE | II 0001-N   90N |
| | FAT BODY TYPE | II 0001-O   90O |
| KNEE/ FLEXED POSITION/ SIDE | THIN BODY TYPE | II 0020-S   91, 90S |
| | NORMAL BODY TYPE | II 0020-N   90N |
| | FAT BODY TYPE | II 0020-O   90O |

130

RADIOGRAPHY SYSTEM AND METHOD FOR OPERATING RADIOGRAPHY SYSTEM

CROSS-REFERENCE TO RELATED APPLICATION

This application claims priority under 35 USC 119 from Japanese Patent Application No. 2017-156067, filed 10 Aug. 2017, the disclosure of which is incorporated by reference herein.

BACKGROUND OF THE INVENTION

1. Field of the Invention

The present invention relates to a radiography system and a method for operating the radiography system.

2. Description of the Related Art

In a medical field, a diagnosis is made on the basis of a radiographic image obtained by a radiography system. The radiography system includes a radiation generation apparatus and a radiography apparatus. The radiation generation apparatus includes a radiation source and the radiography apparatus includes a radiographic image detection device. The radiographic image detection device includes a sensor panel. The sensor panel is provided with an imaging region. A plurality of pixels are two-dimensionally arranged in the imaging region. The pixel is sensitive to radiation which has been emitted from the radiation source and then transmitted through a subject (patient) and accumulates charge. The radiographic image detection device converts the charge accumulated in the pixel into a digital signal and outputs the digital signal as a radiographic image.

The radiographic image detection devices are classified into a fixed type that is fixed to an imaging stand installed in an imaging room and a portable type in which, for example, a sensor panel is accommodated in a portable housing. The portable radiographic image detection device is referred to as an electronic cassette. The electronic cassettes are classified into a wired type that is supplied with power from a commercial power supply through a cable and a wireless type that is supplied with power from a battery provided in a housing.

The electronic cassette is carried out of the imaging room and is then used since it has high mobility. For example, the electronic cassette is used for visit imaging in which an operator visits a hospital room in which a patient who is not able to move to the imaging room is present and takes a radiographic image. In addition, the electronic cassette is used in places other than medical facilities in order to capture a radiographic image of an aged person who gets medical treatment at home or a patient who is in an emergency situation due to an accident or a disaster. Hereinafter, imaging without using an imaging stand is referred to as free imaging.

In a preparation operation before radiography, an operator, such as a radiology technician, relatively positions a radiation source, an electronic cassette, and a patient. After positioning is completed, the operator operates the radiation source to emit radiation and takes a radiographic image.

JP2013-048740A and JP1994-217973A (JP-H06-217973A, corresponding to U.S. Pat. No. 5,539,798A) do not relate to free imaging, but relate to imaging using an imaging stand. However, JP2013-048740A and JP1994-217973A (JP-H06-217973A) disclose a technique that assists positioning and improves the efficiency of a positioning operation. JP2013-048740A discloses an imaging stand in which a C-type arm provided with a radiation source and a fixed radiographic image detection device is attached to a bed on which a patient lies supine. JP1994-217973A (JP-H06-217973A) discloses an imaging stand in which a film cassette is accommodated in a bed on which a patient lies supine. In JP1994-217973A (JP-H06-217973A), the radiation source is attached to the ceiling of an imaging room through the arm. In both JP2013-048740A and JP1994-217973A (JP-H06-217973A), the radiation source and the fixed radiographic image detection device or a film cassette (hereinafter, the two components are collectively referred to as a panel unit for convenience) face each other with the bed interposed therebetween.

Here, in imaging using an imaging stand, first, the patient is moved to the position of the imaging stand. Then, the patient is moved and roughly positioned such that an imaging part of the patient, such as a knee, faces the panel unit of the imaging stand. Then, the irradiation direction or irradiation position of the radiation source is determined such that the imaging part of the patient is included in the irradiation field which is a region irradiated with radiation. In this stage, the positional relationship between the radiation source and the panel unit of the imaging stand is fixed. Then, for example, the position, posture, and direction of the imaging part of the patient are finely adjusted in the irradiation field and positioning is completed. The fine adjustment of the imaging part of the patient is performed by moving the patient with respect to the fixed panel unit as in the rough positioning.

In JP2013-048740A and JP1994-217973A (JP-H06-217973A), a motion picture (hereinafter, referred to as a camera image) captured by an optical camera attached to the radiation source and a positioning index image indicating a position (hereinafter, referred to as a set position) that has been set in advance and is the ideal position of the patient are combined to generate a composite image and the composite image is displayed on a display unit. The field of view of the camera is adjusted such that the center of the camera image is substantially matched with the center of the irradiation field. For example, the display position of the positioning index image of the camera in-image is fixed to a position based on the center of the irradiation field. Specifically, in the positioning index image, the contour of a human body model simulating the imaging part of the patient is represented by lines.

The operator instructs the patient to change the position or posture of the imaging part of the patient such that the position of the imaging part of the patient is matched with the positioning index image or changes the position or posture of the imaging part of the patient with his or her hands while seeing the composite image.

SUMMARY OF THE INVENTION

As described above, JP2013-048740A and JP1994-217973A (JP-H06-217973A) relate to imaging using an imaging stand. Therefore, after the relative position between the radiation source and the panel unit is fixed, the relative positioning between the patient and the panel unit in the irradiation field is performed. Since the position of the radiation source is fixed, the display position of the positioning index image in the camera image is also fixed. The technique disclosed in JP2013-048740A and JP1994-217973A (JP-H06-217973A) can appropriately assist positioning as long as it can move the position or imaging part of the patient on the basis of the positioning index image whose display position is fixed.

However, in free imaging using an electronic cassette, the technique disclosed in JP2013-048740A and JP1994-217973A (JP-H06-217973A) has the problem that it is difficult to appropriately assist positioning. The reason is that, in some cases, the image of the patient who is unable to freely move, such an aged person or a person in an emergency situation, is captured in the free imaging. In this case, it is generally difficult to move the position or posture of an imaging part of the patient with respect to the electronic cassette. In addition, in the free imaging, it is preferable to move the electronic cassette that is easy to handle rather than to move the patient in order to reduce effort. Therefore, in the free imaging, during the relative positioning between the imaging part of the patient and the electronic cassette, the patient is not moved with respect to the electronic cassette, but the electronic cassette is moved with respect to the patient.

In the technique disclosed in JP2013-048740A and JP1994-217973A (JP-H06-217973A), in a state in which the position of the radiation source is fixed, the display position of the positioning index image in the camera image is fixed. Therefore, even in a case in which the electronic cassette corresponding to the panel unit is moved, the display position of the positioning index image in the camera image is fixed as long as the radiation source is not moved. For this reason, the positioning index image disclosed in JP2013-048740A and JP1994-217973A (JP-H06-217973A) is not capable of being used to assist positioning in the free imaging. That is, in a case in which the display position of the positioning index image in the camera image is fixed, the movement of the electronic cassette causes the deviation between the position of the electronic cassette in the camera image and the display position of the positioning index image. In this case, the positioning index image indicating the set position of the imaging part of the patient and the electronic cassette does not have the original function of assisting positioning. Therefore, the technique disclosed in JP2013-048740A and JP1994-217973A (JP-H06-217973A) has the problem that it is difficult to appropriately assist positioning in the free imaging.

An object of the invention is to provide a radiography system that can appropriately assist relative positioning between a subject and an electronic cassette even in free imaging which uses an electronic cassette and does not use an imaging stand and a method for operating the radiography system.

In order to achieve the object, according to an aspect of the invention, there is provided a radiography system comprising: a camera image acquisition unit that, in a case in which radiography is performed using an electronic cassette that detects a radiographic image based on radiation which has been emitted from a radiation source and transmitted through a subject, acquires a camera image obtained by capturing an image of the subject located in an irradiation field which is a region irradiated with the radiation using a camera; a detection unit that detects an in-image cassette position which is a position of the electronic cassette in the camera image, using the camera image; a composite image generation unit that combines the camera image and a positioning index image indicating a set position of the subject, which has been set in advance with respect to the in-image cassette position, to generate a composite image and, in a case in which the in-image cassette position in the camera image is changed with movement of the electronic cassette, changes a display position of the positioning index image in the composite image with the change in the in-image cassette position; and a display controller that performs control such that the composite image is displayed on a display unit.

Preferably, the composite image generation unit displays a cassette position index indicating the position of the electronic cassette in the composite image.

Preferably, in a case in which the electronic cassette is included in the camera image, the detection unit specifies characteristics of the electronic cassette from the camera image and detects the in-image cassette position.

Preferably, the positioning index image is a contour image that indicates a contour of a human body model simulating the subject. Alternatively, it is preferable that the positioning index image is a three-dimensional display image in which the human body model simulating the subject is three-dimensionally displayed.

Preferably, the radiography system further comprises an index image generation unit that generates the positioning index image. In this case, preferably, the index image generation unit generates the positioning index image on the basis of the camera image. Alternatively, it is preferable that the index image generation unit generates the positioning index image on the basis of the radiographic image.

Preferably, in a case in which the positioning index image is a three-dimensional display image, the index image generation unit edits a posture and/or a direction of the subject included in a reference three-dimensional display image on the basis of the camera image to generate an edited three-dimensional display image and uses the generated edited three-dimensional display image as the positioning index image.

Preferably, the radiography system further comprises an index image acquisition unit that accesses an index image database in which a plurality of the positioning index images are registered in advance and acquires the positioning index image.

Preferably, the positioning index image is registered for each imaging menu defining at least one of imaging procedures, which are information related to an imaging part of the subject or a posture and a direction of the imaging part, in the index image database. Preferably, the index image acquisition unit acquires the positioning index image corresponding to the set imaging menu from the index image database.

Preferably, the positioning index image is registered for each subject in the index image database and the index image acquisition unit acquires the positioning index image corresponding to the subject from the index image database.

Preferably, the positioning index image is registered for each body type of the subject in the index image database. Preferably, the radiography system further comprises a body type specification unit that specifies the body type of the subject. Preferably, the index image acquisition unit acquires the positioning index image corresponding to the body type of the subject specified by the body type specification unit from the index image database.

Preferably, the radiography system further comprises: a first calculation unit that calculates a first deviation amount which is an amount of deviation between the set position indicated by the positioning index image and an actual position of the subject; and a first error processing unit that performs first error processing in a case in which the first deviation amount is greater than a predetermined first threshold value.

Preferably, the radiography system further comprises: an association processing unit that associates related information of the positioning index image as accessory information of the radiographic image with the radiographic image.

Preferably, in a case in which long-length imaging that captures each of a plurality of divided imaging ranges, into which a long imaging range including a plurality of imaging parts of the subject is divided, and combines a plurality of the radiographic images corresponding to each divided imaging range to generate a long radiographic image is performed, the detection unit detects the in-image cassette position of the electronic cassette located in a reference divided imaging range and the composite image generation unit displays a recommended cassette position index indicating a recommended position of the electronic cassette in the other divided imaging range with respect to the in-image cassette position of the electronic cassette located in the reference divided imaging range which has been detected by the detection unit.

Preferably, the composite image generation unit displays the positioning index image in the recommended cassette position index.

Preferably, the radiography system further comprises: a second calculation unit that calculates a second deviation amount which is an amount of deviation between the recommended position indicated by the recommended cassette position index and an actual position of the electronic cassette; and a second error processing unit that performs second error processing in a case in which the second deviation amount is greater than a predetermined second threshold value.

Preferably, the camera is attached to the radiation source.

According to another aspect of the invention, there is provided a method for operating a radiography system. The method comprises: a camera image acquisition step of, in a case in which radiography is performed using an electronic cassette that detects a radiographic image based on radiation which has been emitted from a radiation source and transmitted through a subject, acquiring a camera image obtained by capturing an image of the subject located in an irradiation field which is a region irradiated with the radiation using a camera; a detection step of detecting an in-image cassette position which is a position of the electronic cassette in the camera image, using the camera image; a composite image generation step of combining the camera image and a positioning index image indicating a set position of the subject, which has been set in advance with respect to the in-image cassette position, to generate a composite image and, in a case in which the in-image cassette position in the camera image is changed with movement of the electronic cassette, changing a display position of the positioning index image in the composite image with the change in the in-image cassette position; and a display control step of performing control such that the composite image is displayed on a display unit.

According to the invention, in a case in which the in-image cassette position which is the position of the electronic cassette in the camera image is changed with the movement of the electronic cassette, the display position of the positioning index image indicating the set position of the subject, which has been set in advance, is changed with the change in the in-image cassette position. Therefore, it is possible to provide a radiography system that can appropriately assist the relative positioning between the subject and the electronic cassette even in free imaging that uses the electronic cassette and does not use an imaging stand and a method for operating the radiography system.

BRIEF DESCRIPTION OF THE DRAWINGS

FIG. 10 is a diagram illustrating an index image DB.
FIG. 12 is a diagram illustrating an aspect in which an in-image cassette position is changed with the movement of the electronic cassette and a display position of a positioning index image is changed with the change in the in-image cassette position: (A) of FIG. 12 illustrates a state before the electronic cassette is moved, and (B) of FIG. 12 illustrates a state after the electronic cassette is moved.
FIG. 14 is a diagram illustrating an index image DB according to a second embodiment.
FIG. 16 is a diagram illustrating the function of an index image acquisition unit according to the third embodiment: (A) of FIG. 16 illustrates a case in which a positioning index image is input from an index image generation unit; and (B) of FIG. 16 illustrates an aspect in which a registered positioning index image is replaced with a positioning index image generated by the index image generation unit.
FIG. 20 is a diagram illustrating the function of an index image acquisition unit according to the fifth embodiment: (A) of FIG. 20 illustrates a case in which a positioning index image is input from an index image generation unit; and (B) of FIG. 20 illustrates an aspect in which a registered positioning index image is replaced with a positioning index image generated by the index image generation unit.
FIG. 21 is a diagram illustrating an index image DB according to a sixth embodiment.
FIG. 23 is a diagram illustrating an index image DB according to a seventh embodiment.

DESCRIPTION OF THE PREFERRED EMBODIMENTS

First Embodiment

Figure 1:
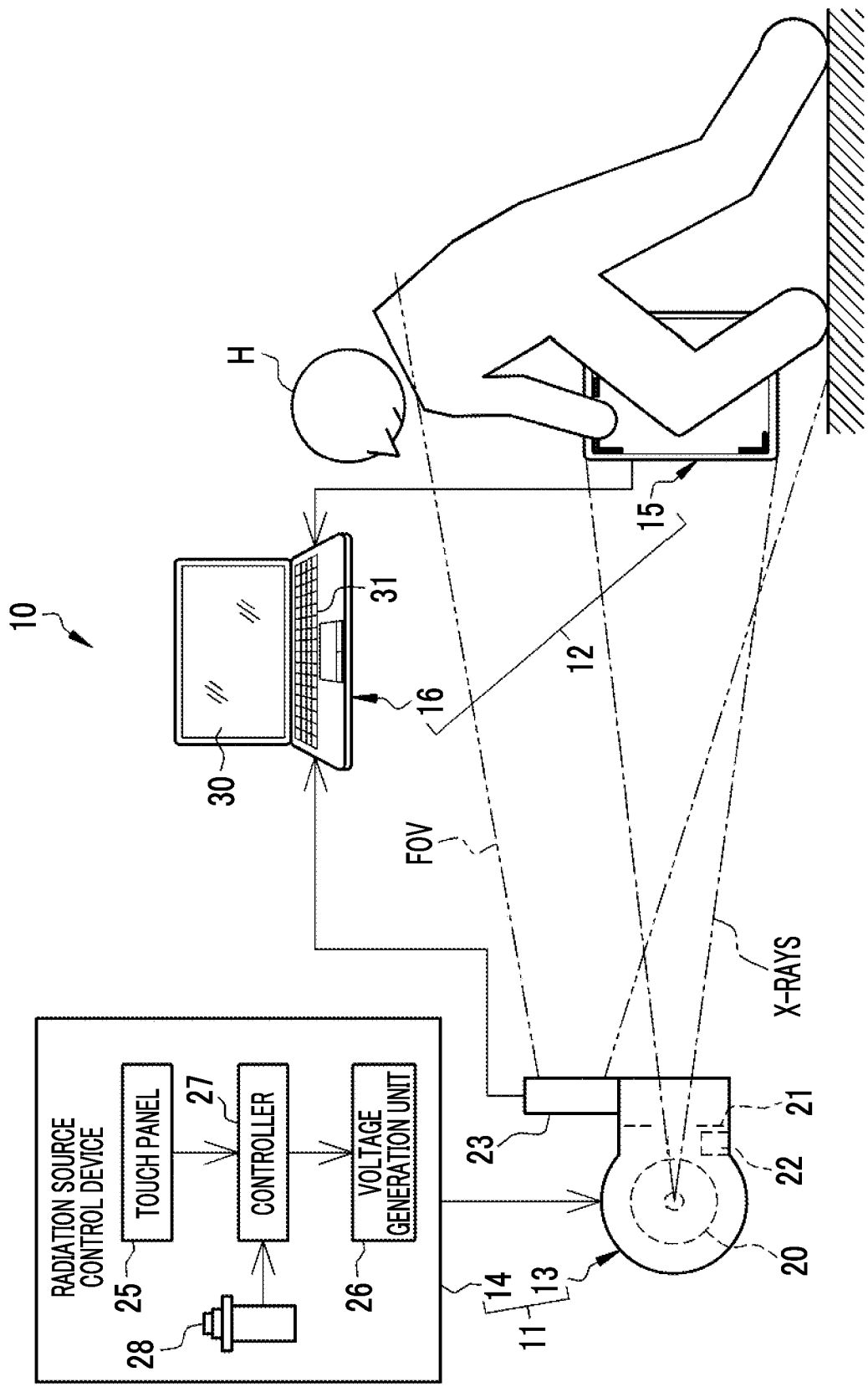
FIG. 1 is a diagram illustrating an X-ray imaging system.

In FIG. 1, an X-ray imaging system 10 that uses X-rays as radiation includes an X-ray generation apparatus 11 and an X-ray imaging apparatus 12. The X-ray generation apparatus 11 includes an X-ray source 13 corresponding to a radiation source and a radiation source control device 14. The X-ray imaging apparatus 12 includes an electronic cassette 15 and a console 16.

FIG. 1 illustrates an aspect in which, in an imaging room in which the X-ray imaging system 10 is installed, a subject H stands at a position facing the X-ray source 13, holds the electronic cassette 15, places the electronic cassette 15 in front of a knee which is an imaging part, and performs X-ray imaging. That is, the X-ray imaging illustrated in FIG. 1 is free imaging without using an imaging stand. Therefore, the electronic cassette 15 is freely movable.

The X-ray source 13 includes an X-ray tube 20 that generates X-rays, an irradiation field limiter 21 that limits an irradiation field which is a region irradiated with X-rays, and an irradiation field display light source 22 that emits irradiation field display light indicating the irradiation field.

The X-ray tube 20 includes a filament that emits thermal electrons and a target that collides with the thermal electrons emitted from the filament and emits X-rays. The irradiation field limiter 21 has, for example, a structure in which four lead plates that shield X-rays are provided on each side of a rectangle and a rectangular irradiation opening which transmits X-rays is provided at the center. In this case, the irradiation field limiter 21 moves the positions of the lead plates to change the size of the irradiation opening, thereby setting the irradiation field. FIG. 1 illustrates a state in which an irradiation field that is substantially the same as an imaging region RX (see FIG. 5) of the electronic cassette 15 is set.

The irradiation field display light source 22 emits the irradiation field display light through the irradiation opening of the irradiation field limiter 21. Therefore, the irradiation field display light literally has the same shape and size as the irradiation field. The irradiation field display light source 22 emits the irradiation field display light of a special color (for example, yellow) such that the operator can visually recognize the irradiation field display light in an imaging room in which the light is dimmed.

An optical camera 23 is attached to the X-ray source 13. The optical axis of the camera 23 is parallel to the emission axis of X-rays passing through the center of the irradiation field. After the operator roughly positions the X-ray source 13, the electronic cassette 15, and the subject H for X-ray imaging, the camera 23 puts the electronic cassette 15 and the subject H into a field of view (hereinafter, referred to as an FOV). The camera 23 captures a camera image 60 (see FIG. 7) which is an optical image including the electronic cassette 15 and the subject H. After the rough positioning, the subject H is located in the irradiation field. Therefore, the camera image 60 is obtained by capturing an image of the subject H located in the irradiation field. The camera image 60 is, for example, a color image and is a motion picture.

Here, a case in which "the camera 23 is attached to the X-ray source 13" includes a case in which the camera 23 is directly attached to a peripheral portion of the X-ray source 13 as illustrated in FIG. 1 and a case in which the camera 23 is provided in the X-ray source 13 like the irradiation field limiter 21 and the irradiation field display light source 22. In addition, the case in which "the camera 23 is attached to the X-ray source 13" includes a case in which an objective lens is provided in a peripheral portion of the X-ray source 13 and an imaging element is provided in a portion (for example, an arm that hangs the X-ray source 13 from the ceiling) other than the X-ray source 13.

The camera 23 includes a wireless communication unit and a battery and is wirelessly operated. The camera 23 wirelessly receives an imaging command signal and an imaging stop signal from the console 16, starts to capture the camera image 60 in response to the imaging command signal, and stops the capture of the camera image 60 in response to the imaging stop signal. The camera 23 wirelessly transmits the captured camera image 60 to the console 16.

The imaging command signal is transmitted from the console 16 to the camera 23 in response to an imaging command input by the operator through an input device 31. The imaging stop signal is automatically transmitted from the console 16 to the camera 23 in a case in which the console 16 receives an irradiation start detection signal informing the start of the emission of X-rays from the electronic cassette 15.

The radiation source control device 14 includes a touch panel 25, a voltage generation unit 26, a controller 27, and an irradiation switch 28. The touch panel 25 is operated in a case in which X-ray emission conditions including a tube voltage and a tube current applied to the X-ray tube 20 and an X-ray emission time and the size of the irradiation opening of the irradiation field limiter 21 are set. Here, the tube current is a parameter for determining the flow rate of thermal electrons emitted from the filament of the X-ray tube 20 to the target.

The voltage generation unit 26 generates the tube voltage to be applied to the X-ray tube 20. The controller 27 controls the operation of the voltage generation unit 26 to control the tube voltage, the tube current, and the X-ray emission time. The controller 27 includes a timer that starts to measure time in a case in which the X-ray tube 20 generates X-rays and stops the operation of the X-ray tube 20 in a case in which the time measured by the timer reaches the irradiation time set in the irradiation conditions. The controller 27 operates the irradiation field limiter 21 such that the size of the irradiation opening is equal to the size set through the touch panel 25.

The irradiation switch 28 is operated by the operator in a case in which the emission of X-rays starts. The irradiation switch 28 is pressed in two stages. In a case in which the irradiation switch 28 is pressed to the first stage (halfway), the controller 27 directs the X-ray tube 20 to start a preparation operation before generating X-rays. In a case in which the irradiation switch 28 is pressed to the second stage (fully), the controller 27 directs the X-ray tube 20 to generate X-rays. In this way, X-rays are emitted to the knee which is an imaging part of the subject H.

The electronic cassette 15 detects an X-ray image 40 (see FIG. 4) based on the X-rays which have been emitted from the X-ray source 13 and then transmitted through the subject H. Similarly to the camera 23, the electronic cassette 15 includes a wireless communication unit and a battery and is wirelessly operated. The electronic cassette 15 wirelessly transmits the X-ray image 40 to the console 16.

The console 16 is implemented by installing, for example, a control program, such as an operating system, or various application programs in a computer such as a notebook personal computer. The console 16 includes a display 30 corresponding to a display unit and an input device 31, such as a touch pad or a keyboard. The console 16 displays various operation screens with an operation function through a graphical user interface (GUI) on the display 30 and receives various operation commands input from the input device 31 by the operator through various operation screens.

Figure 2:
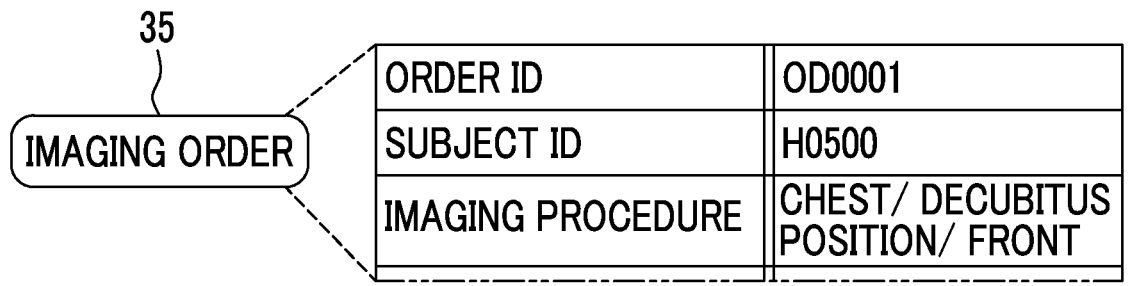
FIG. 2 is a diagram illustrating an imaging order.

The console 16 receives the input of an imaging order 35 illustrated in FIG. 2. The imaging order 35 is, for example, information for commanding the operator to perform X-ray imaging which is received from a person who requests imaging, such as a doctor in a diagnosis and treatment department. The imaging order 35 is transmitted from, for example, a radiology information system (RIS: not illustrated) to the console 16.

The imaging order 35 includes items, such as an order ID (identification data), a subject ID, and an imaging procedure. The order ID is a symbol or a number for identifying each imaging order 35 and is automatically given by the RIS. The subject ID of the subject H that is an imaging target is written in the subject ID item. The subject ID is a symbol or a number for identifying each subject H.

The imaging procedure is information related to an imaging part of the subject H and the posture and direction of the imaging part. Examples of the imaging part include the head, the cervical vertebra, the chest, the abdomen, a hand, a finger, and an elbow, in addition to the knee illustrated in FIG. 1. The posture is the posture of the subject H, such as an upright position, a decubitus position, and a seated position, and the direction is the direction of the subject H with respect to the X-ray source 13, such as the front, the side, and the rear. The imaging order 35 includes subject information items, such as the name, sex, age, height, and weight of the subject H, in addition to the above-mentioned items. In addition, the imaging order 35 includes items, such as a diagnosis and treatment department to which a person who requests imaging belongs, the ID of the person who requests imaging, the date and time when the imaging order 35 is received by the RIS, the purpose of imaging, such as the observation of conditions after the surgery or the determination of the effect of treatment remedies, and orders issued from the person who requests imaging to the operator.

Figure 3:
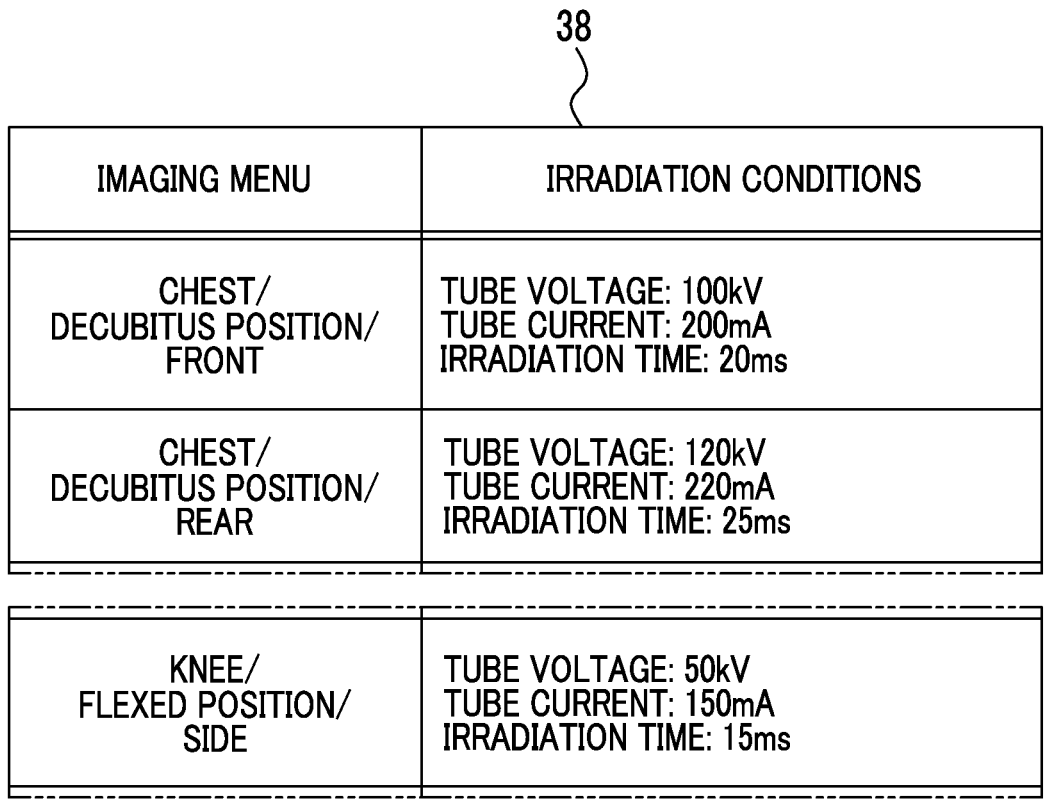
FIG. 3 is a diagram illustrating a menu-condition table.

The console 16 stores a menu-condition table 38 illustrated in FIG. 3. In the menu-condition table 38, an imaging menu for defining an imaging procedure which is a set of an imaging part, a posture, and a direction and irradiation conditions corresponding to the imaging menu are registered so as to be associated with each other. The sets of the imaging menu and the irradiation conditions include a set registered as a default set, a set obtained by the editing of the default set by the operator, and a set which is newly added by the operator and is different from the default set. In addition, the imaging menu may not define the imaging procedure, but may define only the imaging part.

The console 16 is operated by the operator to display an imaging order list which is a list of the content of the imaging order 35 illustrated in FIG. 3 on the display 30. The operator sees the imaging order list and checks the content of the imaging order 35. Then, the console 16 displays the content of the menu-condition table 38 illustrated in FIG. 3 on the display 30 in a form in which the imaging menu can be set. The operator selects an imaging menu matched with the imaging procedure designated by the imaging order 35 and sets the imaging menu.

The console 16 wirelessly transmits a condition setting signal including various kinds of information, such as the imaging menu set by the operator, the irradiation conditions corresponding to the set imaging menu, the order ID, and a console ID which is a symbol or a number for identifying the console 16, to the electronic cassette 15.

Figure 4:
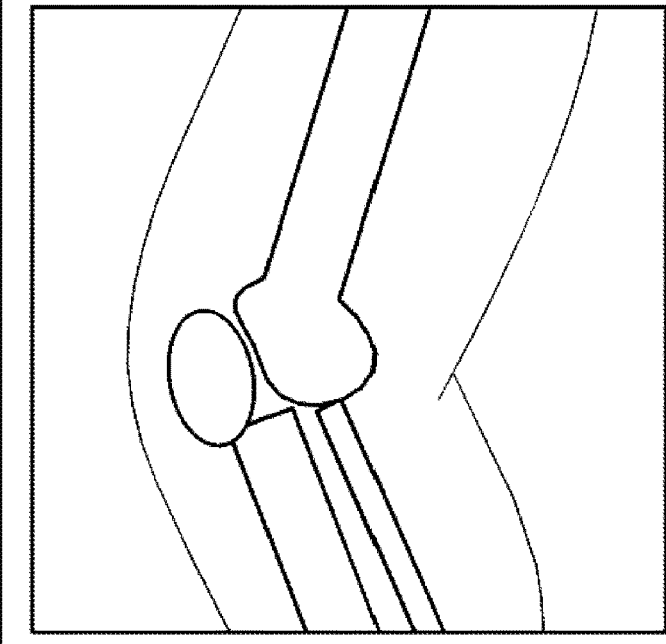
FIG. 4 is a diagram illustrating an image file.

For example, the console 16 converts the X-ray image 40 into an image file 41 in the format based on a Digital Imaging and Communication in Medicine (DICOM) standard illustrated in FIG. 4. Then, the console 16 transmits the image file 41 to a picture archiving and communication system (PACS) (not illustrated).

In the image file 41, the X-ray image 40 and accessory information 42 are associated with each other by one image ID. The accessory information 42 includes, for example, subject information, an order ID, an imaging menu, and irradiation conditions. The person who requests imaging can access the PACS with a client terminal, download the image file 41, and see the X-ray image 40 with the client terminal.

Figure 5:
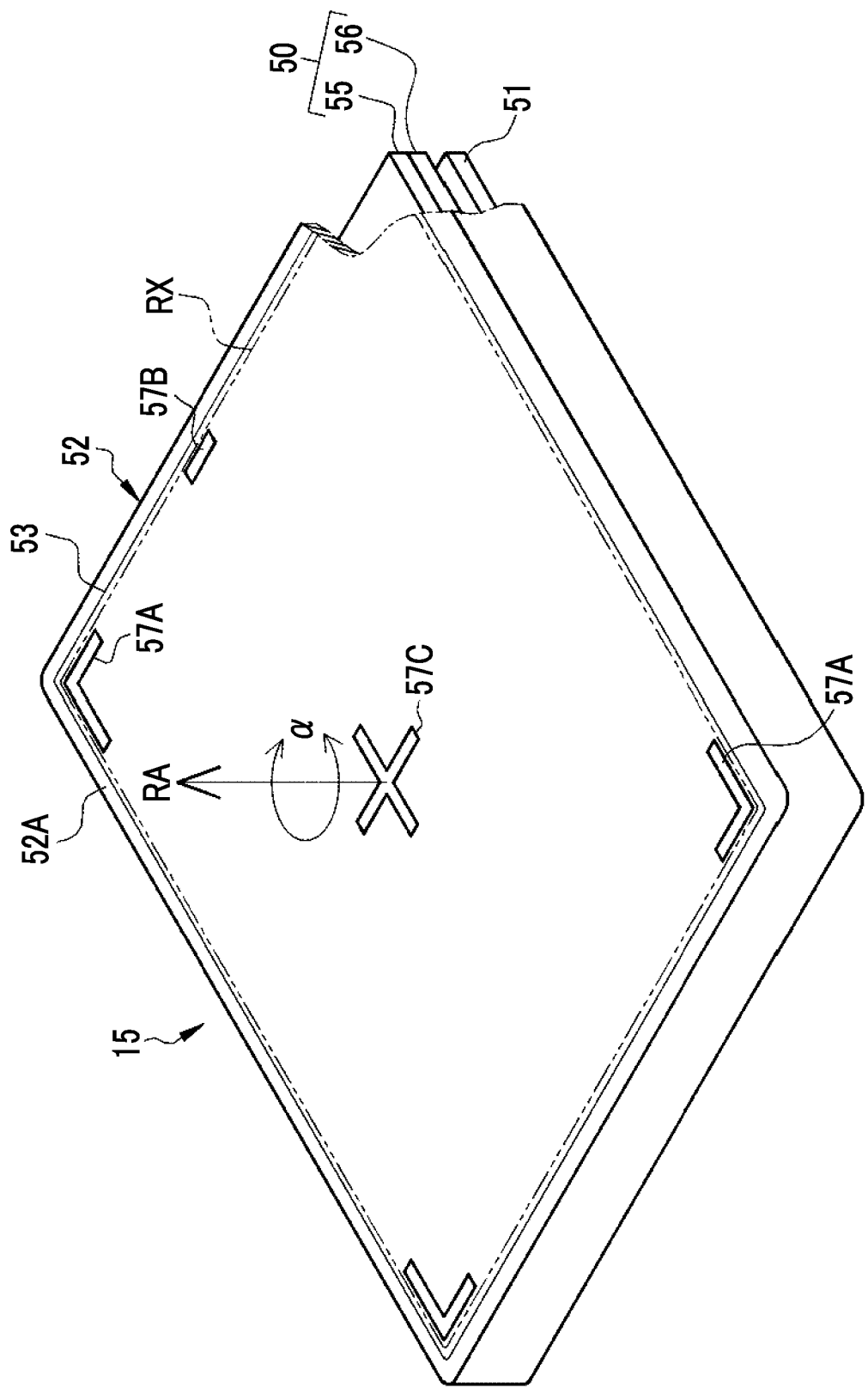
FIG. 5 is a perspective view illustrating the outward appearance of an electronic cassette.

In FIG. 5, the electronic cassette 15 includes a sensor panel 50, a circuit unit 51, and a portable housing 52 having a rectangular parallelepiped shape capable of accommodating the sensor panel 50 and the circuit unit 51. The housing 52 has a size based on International Organization for Standardization (ISO) 4090:2001 which is substantially equal to the size of a film cassette, an imaging plate (IP) cassette, or a computed radiography (CR) cassette.

A rectangular opening is formed in the front surface 52A of the housing 52 and a transmission plate 53 that transmits X-rays is attached to the opening. The electronic cassette 15 is positioned such that the front surface 52A faces the X-ray source 13 and the front surface 52A is irradiated with X-rays. In addition, the housing 52 is provided with a switch for turning on or off a main power supply and an indicator indicating the operating state of the electronic cassette 15 such as the remaining operating time of the battery or the completion state of preparation for imaging.

The sensor panel 50 includes a scintillator 55 and an optical detection substrate 56. The scintillator 55 and the optical detection substrate 56 are stacked in the order of the scintillator 55 and the optical detection substrate 56 as viewed from the front surface 52A. The scintillator 55 has a phosphor, such as CsI:Tl (thallium-activated cesium iodide) or GOS ($Gd_2O_2S$:Tb, terbium-activated gadolinium oxysulfide), converts the X-rays incident through the transmission plate 53 into visible light, and emits the visible light. In addition, a sensor panel may be used in which the optical detection substrate 56 and the scintillator 55 are stacked in this order as viewed from the front surface 52A irradiated with the X-rays. Furthermore, a direct-conversion-type sensor panel may be used which directly converts the X-rays into signal charge using a photoconductive film such as an amorphous selenium film.

The optical detection substrate 56 detects the visible light emitted from the scintillator 55 and converts the visible light into charge. The circuit unit 51 controls the driving of the optical detection substrate 56 and generates the X-ray image 40 on the basis of the charge output from the optical detection substrate 56.

An imaging region RX is provided in the optical detection substrate 56. The imaging region RX has a size that is substantially equal to the size of the transmission plate 53 and includes a plurality of pixels which are arranged in a two-dimensional matrix of N rows and M columns. The pixel is sensitive to the visible light from the scintillator 55 and accumulates charge. The circuit unit 51 converts the charge accumulated in the pixel into a digital signal to detect the X-ray image 40.

Here, N and M are integers that are equal to or greater than 2. For example, N and M are about 2000. In addition, the number of pixels in the matrix is not limited thereto. The array of the pixels may be a square array. Alternatively, the pixels may be inclined at 45° and may be arranged in zigzag.

L-shaped markers 57A are provided at four corners of the imaging region RX. In addition, a rod-shaped marker 57B is provided at the center of a short side of the imaging region RX. The side on which the rod-shaped marker 57B is provided is the upper side of the X-ray image 40. Furthermore, a cross-shaped marker 57C is provided at the center of the imaging region RX. The marker 57A is formed such that a long side is longer than a short side. The position and direction of the imaging region RX are known by the markers 57A to 57C.

The electronic cassette 15 has a function of detecting the start of the emission of X-rays. For example, the irradiation start detection function is implemented by providing an irradiation start detection sensor in the imaging region RX of the optical detection substrate 56. Then, a dose signal corresponding to the amount of X-rays reaching the imaging region, which is output from the irradiation start detection sensor with a predetermined sampling period, is compared with a predetermined irradiation start detection threshold value. In a case in which the dose signal is greater than the irradiation start detection threshold value, it is determined that the emission of X-rays has been started. For example, some of the pixels take charge of the irradiation start detection sensor.

In addition, the electronic cassette 15 includes a timer that starts to measure time in a case in which the start of the emission of X-rays has been detected, similarly to the controller 27 of the radiation source control device 14. In a case in which the time measured by the timer reaches the irradiation time in the irradiation conditions set by the console 16, the electronic cassette 15 determines that the emission of X-rays has ended.

Figure 6:
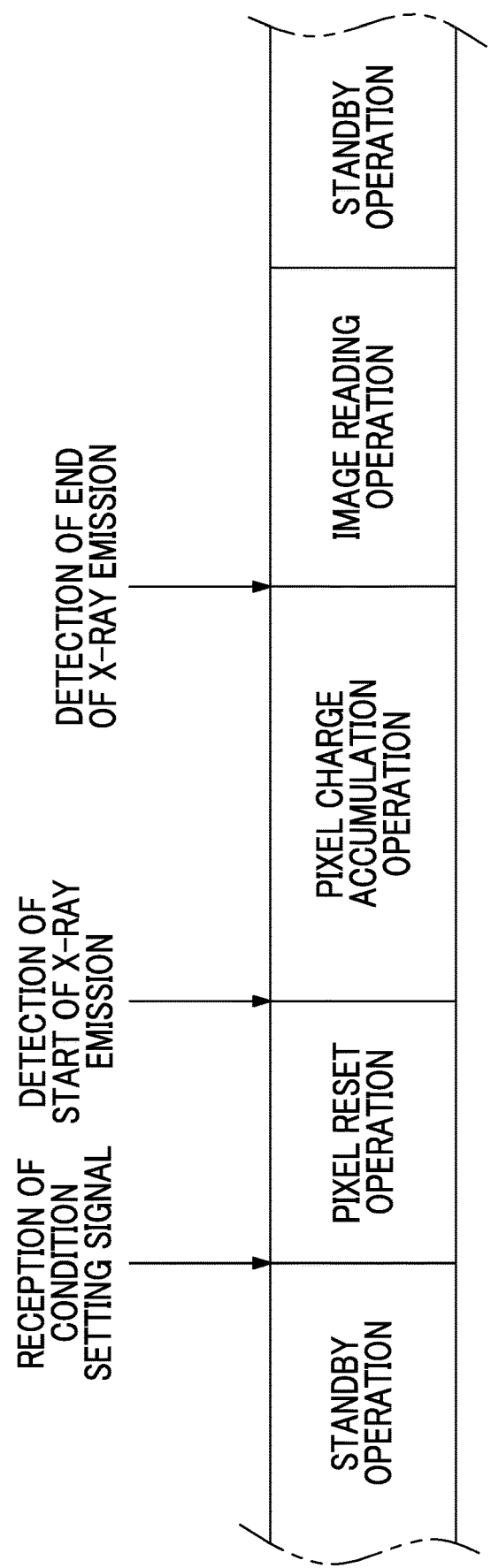
FIG. 6 is a diagram illustrating the flow of an operation performed by the electronic cassette.

As illustrated in FIG. 6, in a case in which the condition setting signal is received from the console 16, the electronic cassette 15 starts a pixel reset operation that reads dark charge from the pixel and resets (discards) the pixel. The electronic cassette 15 performs a standby operation before receiving the condition setting signal. The standby operation supplies power to only a minimum number of necessary units such as a wireless communication unit receiving the condition setting signal.

Then, in a case in which the start of the emission of X-rays has been detected by the irradiation start detection function, the electronic cassette 15 ends the pixel reset operation and starts a pixel charge accumulation operation that accumulates charge corresponding to the amount of X-rays reaching the pixel in the pixel. In this way, it is possible to synchronize the emission start time of X-rays from the X-ray source 13 with the start time of the pixel charge accumulation operation.

In addition, in a case in which the start of the emission of X-rays has been detected by the irradiation start detection function, the electronic cassette 15 wirelessly transmits an irradiation start detection signal indicating that the start of the emission of X-rays has been detected to the console 16.

Then, in a case in which the end of the emission of X-rays has been detected by the timer, the electronic cassette 15 ends the pixel charge accumulation operation and starts an image reading operation for reading the X-ray image 40 to be used for diagnosis. In this way, one X-ray imaging operation for obtaining the X-ray image 40 corresponding to a single screen is completed. After the image reading operation ends, the electronic cassette 15 returns to the standby operation again.

Figure 7:
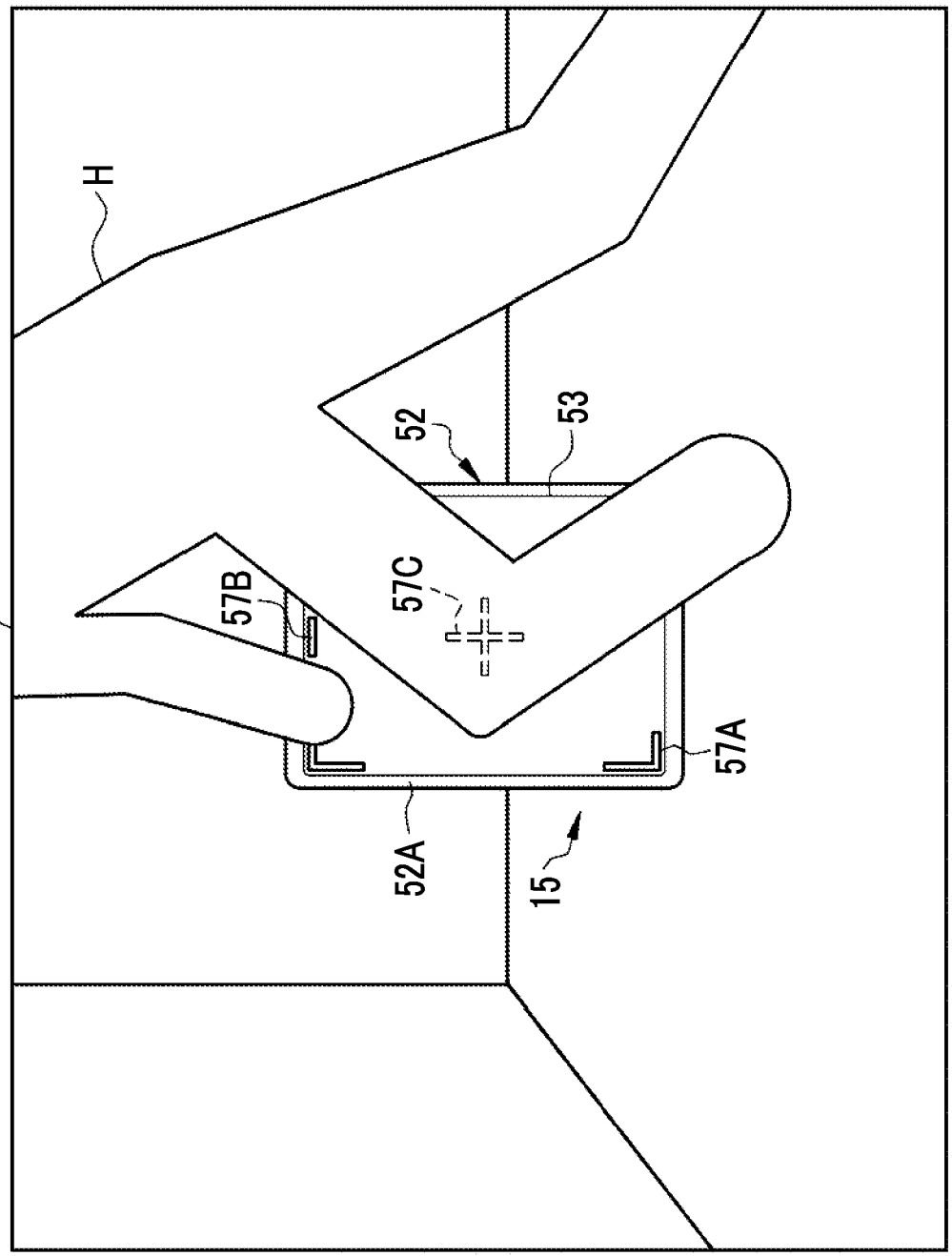
FIG. 7 is a diagram illustrating a camera image.

FIG. 7 illustrates the camera image 60 indicating an aspect of X-ray imaging illustrated in FIG. 1. The camera image 60 includes the lower half of the body of the subject H that bends the knees, a portion of the upper half of the body, and the electronic cassette 15 that is held by the subject H and is placed behind the knee. The electronic cassette 15 is disposed such that the front surface 52A faces the X-ray source 13 and the optical axis of the camera 23 is parallel to the emission axis of X-rays. Therefore, the front surface 52A is included in the camera image 60. In a case in which the irradiation field display light source 22 emits the irradiation field display light, which is not illustrated, the irradiation field display light is also included in the camera image 60.

Since the camera 23 is attached to the X-ray source 13, the positional relationship between the X-ray source 13 and the camera 23 does not vary. Therefore, in the camera image 60, the center of the irradiation field is always located at the same position (for example, the center).

Figure 8:
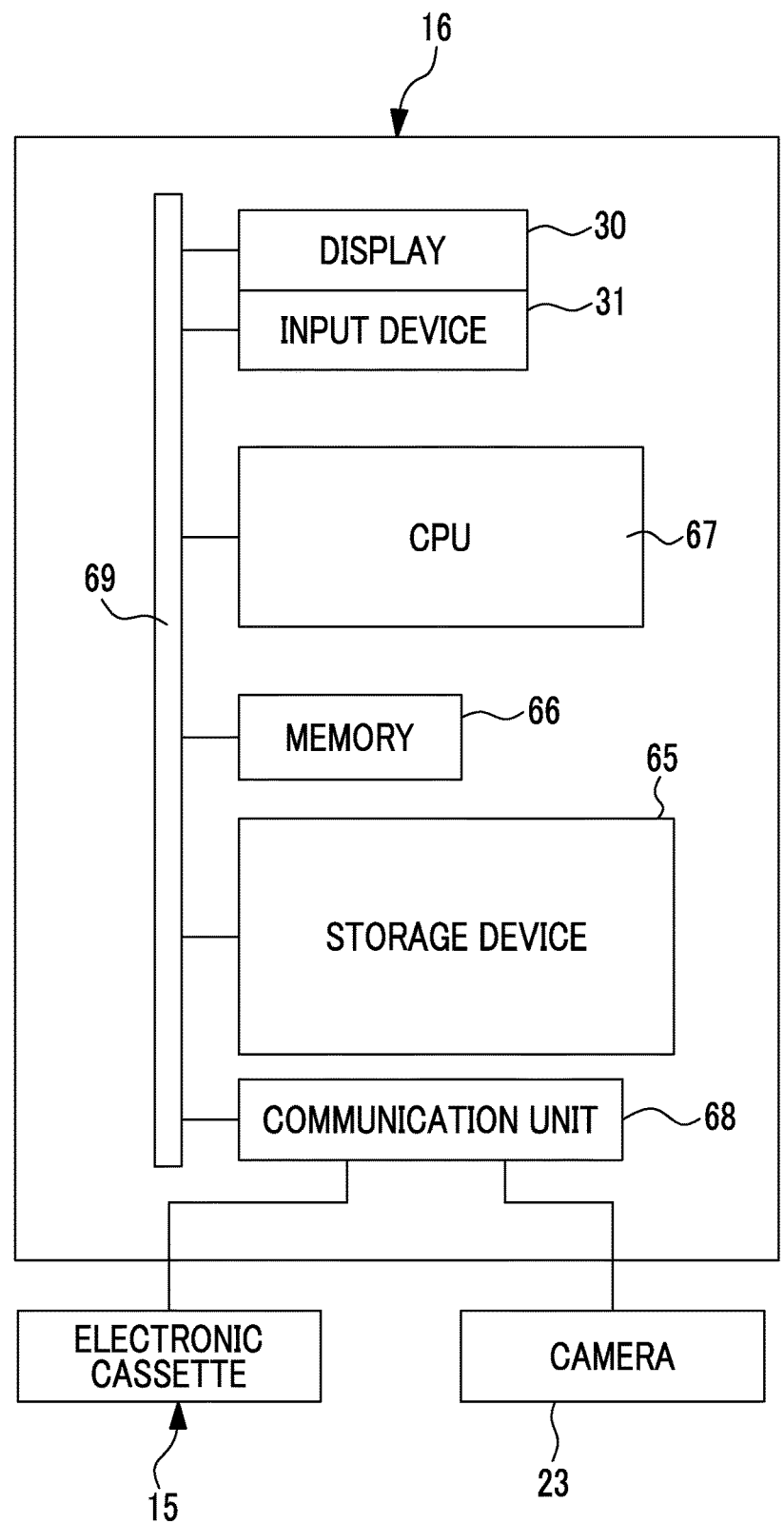
FIG. 8 is a block diagram illustrating a computer forming a console.

In FIG. 8, the console 16 includes a storage device 65, a memory 66, a central processing unit (CPU) 67, and a communication unit 68 in addition to the display 30 and the input device 31. These units are connected to each other through a data bus 69.

The storage device 65 is a hard disk drive or a disk array of a plurality of hard disk drives which is provided in the console 16 or is connected to the console 16 through a cable or a network. For example, the storage device 65 stores a control program, such as an operating system, various application programs, and various kinds of data associated with the programs.

The memory 66 is a work memory that is used by the CPU 67 to perform processes. The CPU 67 loads the program stored in the storage device 65 to the memory 66 and performs the process corresponding to the program to control the overall operation of each unit of the console 16. The communication unit 68 communicates with the electronic cassette 15 and the camera 23 to transmit and receive various kinds of data such as the X-ray image 40 and the camera image 60.

Figure 9:
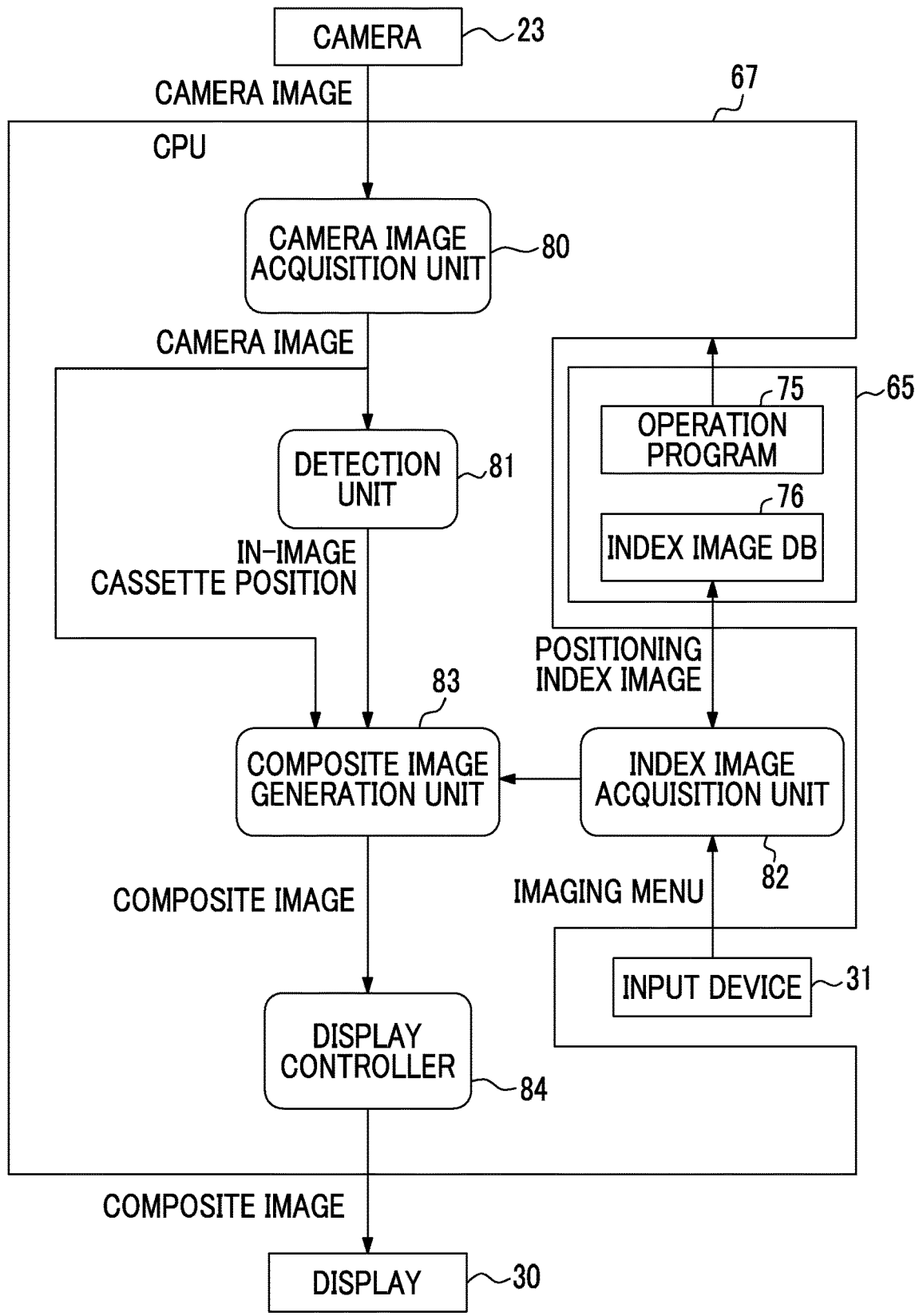
FIG. 9 is a block diagram illustrating a CPU of the console.

In FIG. 9, the storage device 65 stores an operation program 75 and an index image database (hereinafter, abbreviated to DB) 76. The storage device 65 also stores the menu-condition table 38 illustrated in FIG. 3, which is not illustrated.

In a case in which the operation program 75 is run, the CPU 67 functions as a camera image acquisition unit 80, a detection unit 81, an index image acquisition unit 82, a composite image generation unit 83, and a display controller 84 in cooperation with, for example, the memory 66.

The camera image acquisition unit 80 has a camera image acquisition function of acquiring the camera image 60 from the camera 23. The camera image acquisition unit 80 outputs the acquired camera image 60 to the detection unit 81 and the composite image generation unit 83.

The detection unit 81 has a detection function of detecting an in-image cassette position which is the position of the electronic cassette 15 in the camera image 60 on the basis of the camera image 60. Specifically, in a case in which the electronic cassette 15 is included in the camera image 60 as illustrated in FIG. 7, the detection unit 81 applies a known image recognition technique to the camera image 60 to specify the markers 57A to 57C on the front surface 52A of the housing 52 of the electronic cassette 15 as the characteristics of the electronic cassette 15. Then, the detection unit 81 detects the position coordinates of the specified markers 57A to 57C in the camera image 60 as the in-image cassette position. The detection unit 81 outputs the detected in-image cassette position to the composite image generation unit 83.

In this example, of course, the marker 57C which is covered by the subject H and is not included in the camera image 60 is not recognized by the detection unit 81 as illustrated in FIG. 7. However, in a case in which at least one of the four markers 57A can be specified, it is possible to detect the in-image cassette position. Instead of or in addition to the markers 57A to 57C, the contour of the periphery of the front surface 52A may be specified as the characteristics of the electronic cassette 15.

The index image acquisition unit 82 accesses the index image DB 76 and acquires a positioning index image 90 (see FIG. 10) indicating the set position of the subject H which has been set in advance with respect to the in-image cassette position. The index image acquisition unit 82 outputs the acquired positioning index image 90 to the composite image generation unit 83. The set position is the ideal position of the subject H with respect to the in-image cassette position and is set before X-ray imaging, that is, is set in advance.

Figure 11:
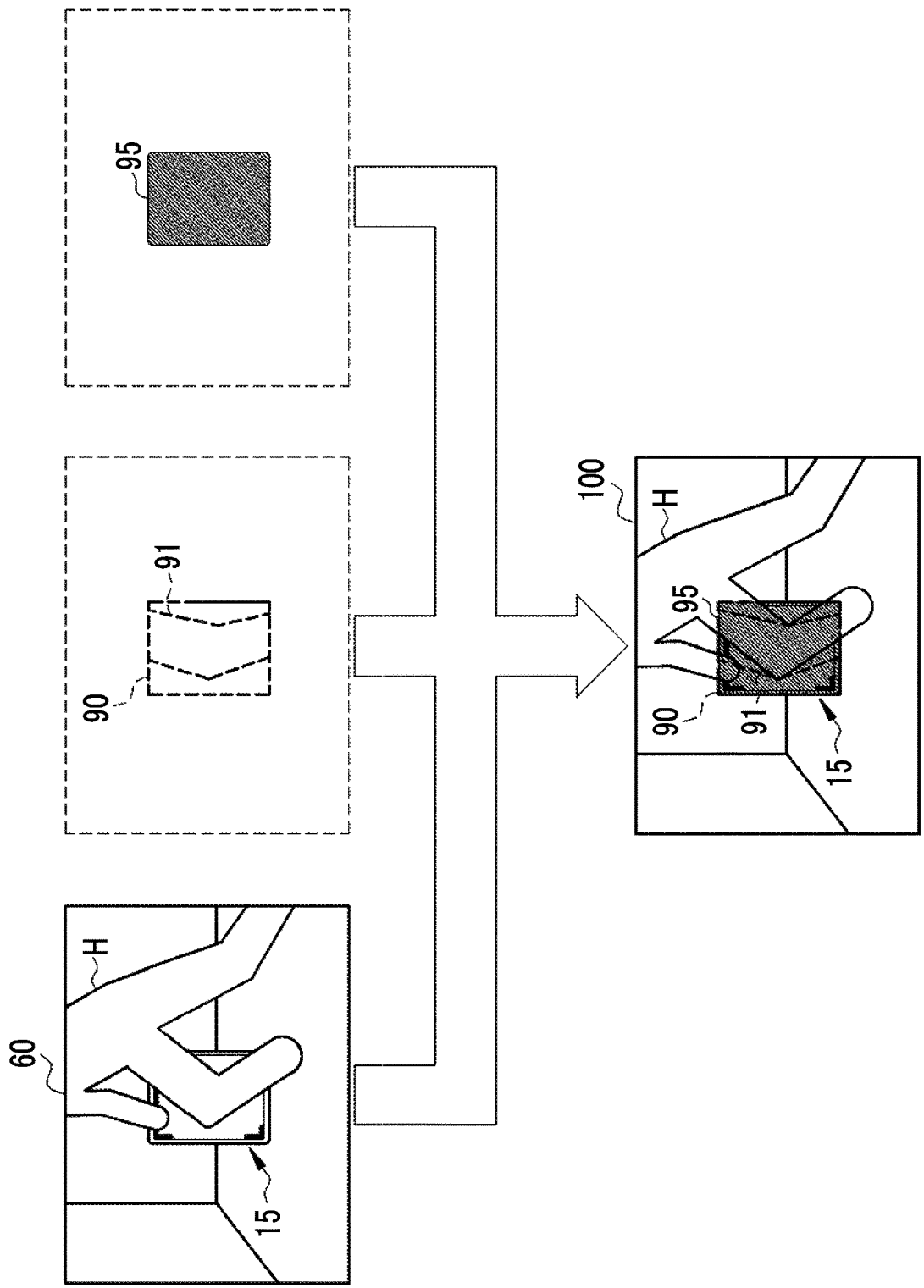
FIG. 11 is a diagram illustrating the generation of a composite image.

The composite image generation unit 83 has a composite image generation function of combining the camera image 60 from the camera image acquisition unit 80 and the positioning index image 90 from the index image acquisition unit 82 to generate a composite image 100 (see FIG. 11). In addition, the composite image generation unit 83 displays a cassette frame 95 (see FIG. 11) as a cassette position index indicating the position of the electronic cassette 15 on the composite image 100. The composite image generation unit 83 outputs the generated composite image 100 to the display controller 84.

The display controller 84 has a display control function of controlling the display of the composite image 100 from the composite image generation unit 83 on the display 30.

The units 80 to 84 start to operate in a case in which the imaging command signal has been transmitted to the camera 23 through the communication unit 68 and continuously operate until the imaging stop signal is transmitted to the camera 23 through the communication unit 68. Then, in a case in which the imaging stop signal has been transmitted, the units 80 to 84 stop their operations. That is, the units 80 to 84 operate only for a period from the transmission of the imaging command signal to the camera 23 to the transmission of the imaging stop signal. Therefore, the composite image 100 is displayed on the display 30 only for the period.

As illustrated in FIG. 10, the positioning index image 90 is registered for each imaging menu in the index image DB 76. The positioning index image 90 is registered together with an index image ID, such as II0001, which is a symbol or a number for identifying each positioning index image 90.

The positioning index image 90 is a contour image which has a shape similar to the shape of the front surface 52A of the electronic cassette 15 and in which the contour 91 of a human body model simulating each imaging part of the subject H is represented by a dashed line.

For example, positioning index images 90 which have index image IDs II0001 and II0002 and indicate the contour 91 of a human body model simulating the upper half of the body of the subject H including the chest are registered for an imaging menu "chest/decubitus position/front" and an imaging menu "chest/decubitus position/rear", respectively. In addition, a positioning index image 90 which has an index image ID II0020 and indicates the contour 91 of a human body model simulating a central portion of the leg of the subject H including the knee is registered for an imaging menu "knee/flexed position/side". The index image acquisition unit 82 acquires the positioning index image 90 corresponding to the imaging menu, which has been set by the operator through the input device 31, from the index image DB 76. In addition, the positioning index image 90 may be registered in the menu-condition table 38 illustrated in FIG. 3 and the menu-condition table 38 and the index image DB 76 may be integrated into one data item.

As illustrated in FIG. 11, the composite image generation unit 83 combines the camera image 60, the positioning index image 90, and the cassette frame 95 to generate the composite image 100. The composite image generation unit 83 calculates four corners of the front surface 52A of the electronic cassette 15 on the basis of the in-image cassette position from the detection unit 81 and connects the calculated four corners with straight lines to generate the cassette frame 95. Therefore, the cassette frame 95 has a rectangular shape simulating the outward shape of the front surface 52A. In addition, the composite image generation unit 83 paints the inside of the rectangular cassette frame 95 in a specific light color, for example, light green such that the background is transparent, as represented by hatching.

The composite image generation unit 83 edits the positioning index image 90 from the index image acquisition unit 82 on the basis of the in-image cassette position from the detection unit 81 during the combination with the camera image 60. Specifically, the composite image generation unit 83 calculates a rotation angle α (see FIG. 5) about a normal line RA (see FIG. 5) to the front surface 52A of the electronic cassette 15 from the in-image cassette position and rotates the positioning index image 90 by the calculated rotation angle. In addition, the composite image generation unit 83 calculates the size of the electronic cassette 15 included in the camera image 60 from the in-image cassette position. Then, the composite image generation unit 83 enlarges or reduces the size of the positioning index image 90 so as to be equal to the calculated size of the electronic cassette 15. Then, the frame of the positioning index image 90 is matched with the cassette frame 95. Therefore, the cassette frame 95 is not displayed and the positioning index image 90 may also function as the cassette frame 95.

In a case in which the in-image cassette position in the camera image 60 is changed with the movement of the electronic cassette 15 as illustrated in FIG. 12, the composite image generation unit 83 changes the display position of the positioning index image 90 in the composite image 100 with the change in the in-image cassette position. The composite image generation unit 83 changes the display position of the cassette frame 95 as well as the display position of the positioning index image 90 with the change in the in-image cassette position. (A) of FIG. 12 illustrates a case in which the electronic cassette 15 is located on the left side of the knee of the subject H and (B) of FIG. 12 illustrates a case in which the electronic cassette 15 is drawn to the right knee.

(A) of FIG. 12 illustrates only a case before the electronic cassette 15 is moved (before the in-image cassette position is changed) and (B) of FIG. 12B illustrates only a case after the electronic cassette 15 is moved (after the in-image cassette position is changed). However, while the electronic cassette 15 is being moved, the composite image generation unit 83 smoothly changes the display position of the positioning index image 90 and the cassette frame 95 with the change in the in-image cassette position.

Figure 13:
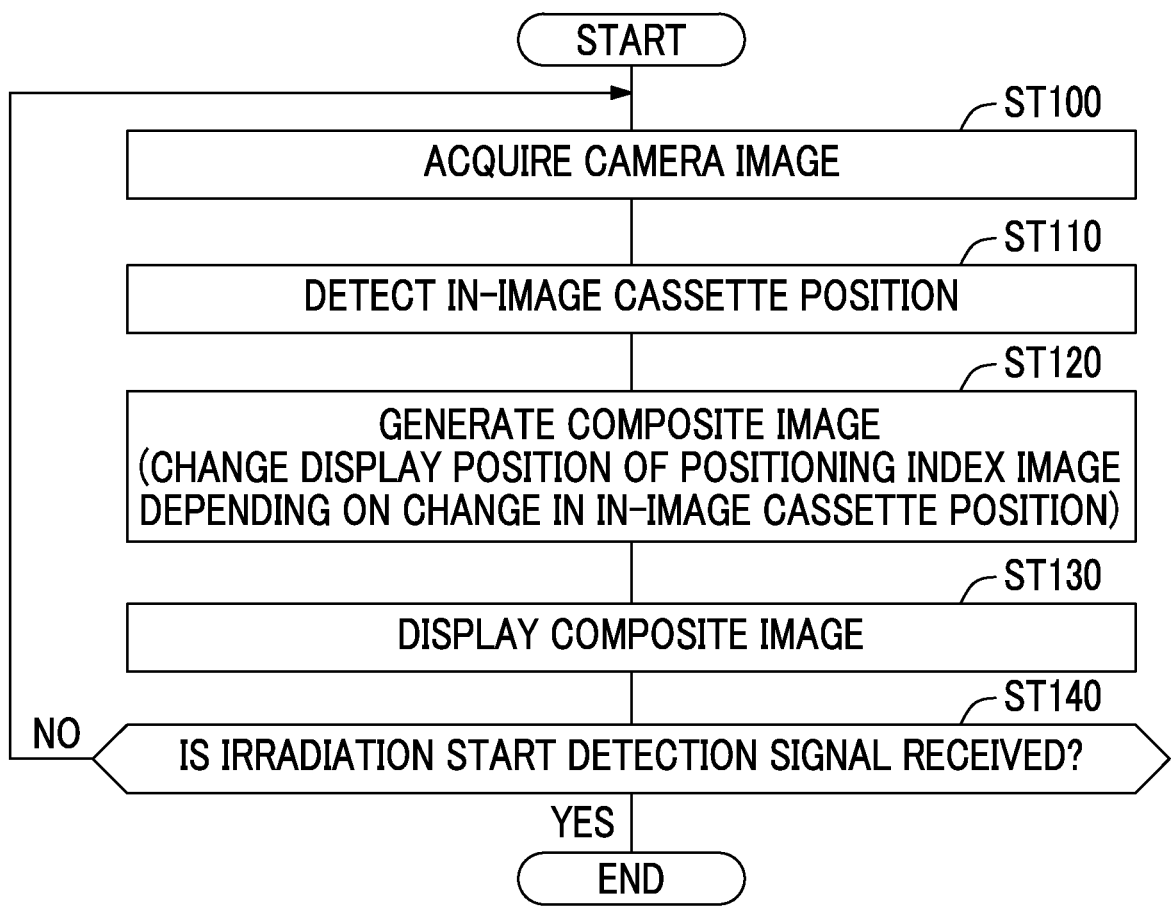
FIG. 13 is a flowchart illustrating the procedure of the process of the CPU of the console.

Next, the operation of the above-mentioned configuration will be described with reference to the flowchart illustrated in FIG. 13. First, the operator checks the content of the imaging order 35 on the display 30 and sets a desired imaging menu corresponding to the imaging order 35 through the input device 31. Then, a condition setting signal including, for example, the set imaging menu and the irradiation conditions corresponding to the imaging menu is transmitted from the console 16 to the electronic cassette 15. After setting the imaging menu, the operator sets the same irradiation conditions as the irradiation conditions corresponding to the set imaging menu to the radiation source control device 14 through the touch panel 25. Then, the operator starts to relatively position the X-ray source 13, the electronic cassette 15, and the subject H.

The operator inputs a command to capture the camera image 60 through the input device 31. Then, the imaging command signal to capture the camera image 60 is wirelessly transmitted from the console 16 to the camera 23. The camera 23 receives the imaging command signal and starts to capture the camera image 60. In addition, as illustrated in FIG. 9, in the CPU 67 of the console 16, the camera image acquisition unit 80, the detection unit 81, the index image acquisition unit 82, the composite image generation unit 83, and the display controller 84 start to operate.

For example, in a case in which the image of the knee is captured, the operator instructs the subject H to hold the electronic cassette 15 and to place the electronic cassette 15 behind the knee, as illustrated in FIG. 1. In addition, the operator sets the X-ray source 13 at a position facing the knee of the subject H. In this case, the operator sets the size of the irradiation opening of the irradiation field limiter 21, that is, the irradiation field to the radiation source control device 14 through the touch panel 25.

The operator operates the irradiation field display light source 22 to emit the irradiation field display light to the electronic cassette 15. The operator finely adjusts the position on the basis of the irradiation field display light such that the desired positional relationship is established between the X-ray source 13, the electronic cassette 15, and the subject H.

The camera 23 captures the aspect of the positioning by the operator. As illustrated in Step ST100 of FIG. 13, the camera image acquisition unit 80 acquires the camera image 60 captured by the camera 23 (camera image acquisition step). The camera image 60 is output from the camera image acquisition unit 80 to the detection unit 81 and the composite image generation unit 83.

The detection unit 81 detects the in-image cassette position which is the position of the electronic cassette 15 in the camera image 60 from the camera image acquisition unit 80 (Step ST110: a detection step). The index image acquisition unit 82 acquires the positioning index image 90 corresponding to the imaging menu set by the operator from the index image DB 76 and outputs the positioning index image 90 to the composite image generation unit 83.

In Step ST120, the composite image generation unit 83 combines the camera image 60 from the camera image acquisition unit 80, the positioning index image 90 from the index image acquisition unit 82, and the cassette frame 95 to generate the composite image 100 as illustrated in FIG. 11 (composite image generation step). In this case, in a case in which the in-image cassette position in the camera image 60 is changed with the movement of the electronic cassette 15 as illustrated in FIG. 12, the composite image generation unit 83 changes the display position of the positioning index image 90 in the composite image 100 with the change in the in-image cassette position. The composite image 100 is displayed on the display 30 through the display controller 84 (Step ST130: a display control step). The operator performs positioning while seeing the composite image 100 displayed on the display 30.

After the positioning, the operator operates the irradiation switch 28 such that the X-ray source 13 generates X-rays. The front surface 52A of the electronic cassette 15 is irradiated with the X-rays which have been emitted from the X-ray source 13 and then transmitted through the subject H. The electronic cassette 15 detects the start of the emission of the X-rays using the irradiation start detection function. Then, the irradiation start detection signal is wirelessly transmitted from the electronic cassette 15 to the console 16. Then, a signal for stopping the capture of the camera image 60 is wirelessly transmitted from the console 16 to the camera 23. The camera 23 receives the imaging stop signal and stops the capture of the camera image 60. In addition, the operation of the units 80 to 84 of the CPU 67 is stopped (YES in Step ST140).

After the start of the emission of X-rays is detected, the electronic cassette 15 performs the pixel charge accumulation operation and the image reading operation to detect the X-ray image 40 as illustrated in FIG. 6. The X-ray image 40 is wirelessly transmitted from the electronic cassette 15 to the console 16. The console 16 converts the X-ray image 40 into the image file 41 and transmits the image file 41 to the PACS such that the image file 41 is seen by the person who requests imaging.

The operator compares the set position indicated by the positioning index image 90 in the composite image 100 with the actual position of the subject H to immediately check the degree of matching between the set position and the actual position.

Then, in a case in which the in-image cassette position in the camera image 60 is changed with the movement of the electronic cassette 15, the display position of the positioning index image 90 in the composite image 100 is changed with the change in the in-image cassette position. As such, since the positioning index image 90 follows the movement of the electronic cassette 15, it is possible to appropriately assist positioning in free imaging in which the subject H is not moved with respect to the electronic cassette 15, but the electronic cassette 15 is moved with respect to the subject H.

The positioning index image 90 enables the operator to easily adjust the relative position between the subject H and the electronic cassette 15. Therefore, it is possible to relatively position the subject H and the electronic cassette 15 without any problem in free imaging. In a case in which the subject H and the electronic cassette 15 are relatively positioned without any problem, an imaging error in which a desired imaging part deviates and an image of the imaging part is captured does not occur. Therefore, an unnecessary operation, such as a re-imaging operation, is not performed.

The composite image generation unit 83 displays the cassette frame 95 as the cassette position index in the composite image 100. Therefore, the operator can definitely check the position of the electronic cassette 15 even in a state in which a portion of the electronic cassette 15 is covered by the subject H. As a result, it is possible to further assist the relative positioning between the subject H and the electronic cassette 15 and to further reduce the probability that an imaging error will occur.

In addition, the composite image generation unit 83 may determine whether to combine the cassette frame 95 on the basis of the exposure area of the electronic cassette 15. For example, the composite image generation unit 83 combines the cassette frame 95 and the composite image 100 in a case in which 50 percent or more of the electronic cassette 15 is covered by the subject H and does not combine the cassette frame 95 in a case in which less than 50 percent of the area of the electronic cassette 15 is covered by the subject H.

In a case in which the electronic cassette 15 is included in the camera image 60, the detection unit 81 can specify the markers 57A to 57C or the characteristics of the electronic cassette 15, such as the contour of the periphery of the front surface 52A, using simple image recognition, and detect the in-image cassette position from the camera image 60.

The positioning index image 90 is a contour image indicating the contour of the human body model simulating the subject H. Since the contour of the human body model simulating the subject H is minimum information required for positioning, the positioning index image 90 is simple in display. It is possible to prevent the composite image 100 from being complicated in display.

In the index image DB 76, the positioning index image 90 is registered for each imaging menu. The index image acquisition unit 82 acquires the positioning index image 90 corresponding to the imaging menu set by the operator from the index image DB 76. Therefore, it is possible to perform positioning suitable for each imaging menu.

Since the camera 23 is attached to the X-ray source 13, it is possible to simply put the subject H and the electronic cassette 15 located in the irradiation field into the FOV.

Second Embodiment

In a second embodiment illustrated in FIG. 14, the positioning index image is a three-dimensional display image.

In FIG. 14, a three-dimensional display image in which a human body model simulating the subject H is three-dimensionally displayed is registered as a positioning index image 106 in an index image DB 105 according to this embodiment. In the positioning index image 106, the contour 107 of the human body model simulating each imaging part of the subject H is displayed, similarly to the contour 91 of the positioning index image 90 according to the first embodiment. In addition, lines of wrinkles, such as bent wrinkles behind a knee joint, or lines of bones, such as the sternum, the ribs, the scapula, and the patella, are also displayed. Lines indicating the three-dimensional structure of the body in the positioning index image 106 make it possible to determine the posture and direction of an imaging part of the subject H. In addition, for example, the front and rear sides of the hand can be simply distinguished by parts such as nails included in the display image.

As such, in a case in which the positioning index image 106 which is a three-dimensional display image indicating the three-dimensional posture and direction of the subject H is used, the posture and direction of the subject H are more accurately detected than those in a case in which the positioning index image 90 according to the first embodiment is used. Therefore, it is possible to further improve the accuracy of positioning and to further reduce the probability that an imaging error will occur.

Third Embodiment

Figure 15:
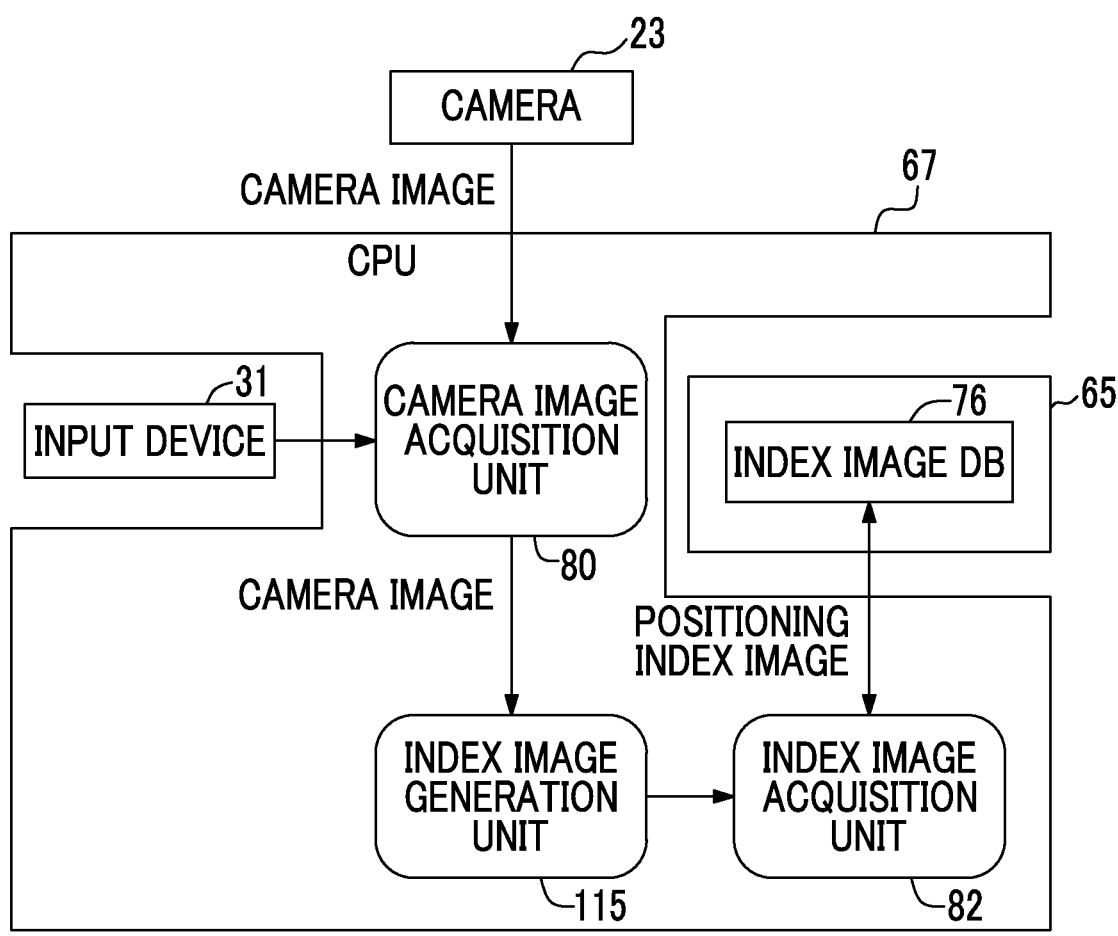
FIG. 15 is a block diagram illustrating a CPU of a console according to a third embodiment.

In a third embodiment illustrated in FIGS. 15 and 16, the positioning index image 90 is generated on the basis of the camera image 60.

In FIG. 15, a CPU 67 of a console 16 according to this embodiment includes an index image generation unit 115 in addition to the units 80 to 84 (only the camera image acquisition unit 80 and the index image acquisition unit 82 are illustrated in FIG. 15) according to the first embodiment illustrated in FIG. 9. In the following embodiments, the units 80 to 84 according to the first embodiment illustrated in FIG. 9 are provided in the CPU 67 unless otherwise noted.

In a case in which the operator inputs an index image generation command through the input device 31, the camera image acquisition unit 80 outputs the acquired camera image 60 to the index image generation unit 115. Similarly to the detection unit 81 according to the first embodiment, the index image generation unit 115 applies a known image recognition technique to the camera image 60 to extract the contour of the subject H included in the camera image 60. Then, the index image generation unit 115 generates the positioning index image 90 on the basis of the extracted contour. Hereinafter, the positioning index image 90 generated by the index image generation unit 115 is referred to as a positioning index image 90G1 in order to distinguish the positioning index image 90G1 from the positioning index image 90 registered in the index image DB 76. The index image generation unit 115 outputs the positioning index image 90G1 to the index image acquisition unit 82.

In this embodiment, as illustrated in FIG. 16, the index image acquisition unit 82 has an index image registration function of registering the positioning index image 90G1 generated by the index image generation unit 115 in the index image DB 76 in addition to the index image acquisition function of acquiring the positioning index image 90 from the index image DB 76.

That is, in a case in which the positioning index image 90G1 is input from the index image generation unit 115 as illustrated in (A) of FIG. 16, the index image acquisition unit 82 replaces the positioning index image 90 registered in the index image DB 76 with the positioning index image 90G1 generated by the index image generation unit 115 as illustrated in (B) of FIG. 16. FIG. 16 illustrates an aspect in which the positioning index image 90 is replaced with the positioning index image 90G1 in which the bending angle of the upper leg with respect to the lower leg is less than that in the positioning index image 90.

As such, the index image generation unit 115 generates the positioning index image 90G1 on the basis of the camera image 60. Therefore, it is possible to update the positioning index image 90 according to the preference of the operator or rules in medical facilities. The camera image 60 is used not only to assist positioning, but also to generate the positioning index image 90G1. Therefore, it is possible to effectively use the camera image 60.

In addition, the camera image 60 may be stored in the storage device 65 and the index image generation unit 115 may extract the contour from the camera image 60 and generate the positioning index image 90G1 whenever the positioning index image 90 is used. However, the amount of data of the camera image 60 is more than the amount of data of the positioning index image 90G1 indicating only the contour. Therefore, in a case in which the camera image 60 is stored, there is a concern that pressure will be applied to the capacity of the storage device 65. In addition, since the optical image of the subject H is included in the camera image 60, there are privacy problems. Furthermore, it takes a lot of time and effort for the index image generation unit 115 to generate the positioning index image 90G1 whenever the positioning index image 90 is used. Therefore, it is preferable to generate the positioning index image 90G1 only once and to store the generated positioning index image 90G1.

The camera image 60 which is the basis of the positioning index image 90G1 is not limited to the camera image 60 acquired in real time in a case in which the index image generation command has been input. The positioning index image 90G1 may be generated on the basis of the camera image 60 acquired by the camera image acquisition unit 80 at the time when the irradiation start detection signal is received from the electronic cassette 15, that is, at the time when the emission of X-rays starts.

In addition, a motion picture of the camera images 60 may be stored in the storage device 65 and the positioning index image 90G1 may be generated on the basis of the camera image 60 corresponding to one frame which is selected by the operator after the motion picture is reviewed by the operator. At that time, a frame in which the set position indicated by the positioning index image 90 clearly deviates from the actual position of the subject H or a frame in which the electronic cassette 15 or the subject H or both the electronic cassette 15 and the subject H are blurred may be removed from the motion picture of the camera images 60 by image processing and the motion picture may be provided so as to be seen by the operator. In this case, the time required for the operator to see the motion picture of the camera images 60 is reduced and the operator can select the camera image 60 corresponding to one frame suitable for generating the positioning index image 90G1.

The index image ID is not illustrated in FIG. 16. However, the index image acquisition unit 82 gives a new index image ID which is different from that of the positioning index image 90 registered in the index image DB 76 to the positioning index image 90G1 generated by the index image generation unit 115. This holds for a positioning index image 90G2 according to the following fourth embodiment and a positioning index image 106G (see FIG. 19) according to the following fifth embodiment.

Fourth Embodiment

Figure 17:
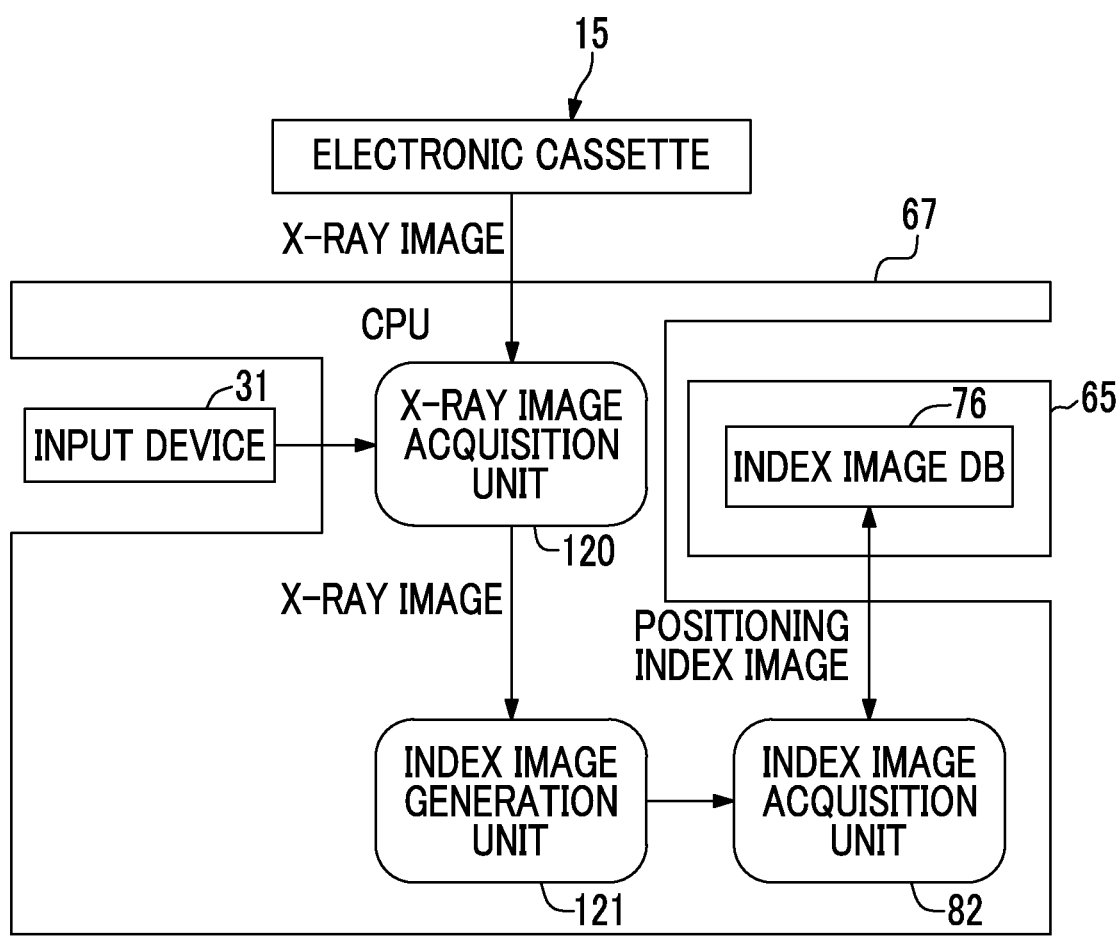
FIG. 17 is a block diagram illustrating a CPU of a console according to a fourth embodiment.

In a fourth embodiment illustrated in FIG. 17, the positioning index image 90 is not generated on the basis of the camera image 60, but is generated on the basis of the X-ray image 40.

In FIG. 17, a CPU 67 of a console 16 according to this embodiment includes an X-ray image acquisition unit 120 and an index image generation unit 121. The X-ray image acquisition unit 120 acquires the X-ray image 40 from the electronic cassette 15. The index image generation unit 121 generates the positioning index image 90 on the basis of the X-ray image 40.

The subsequent processes are basically the same as those in the third embodiment except that the camera image 60 is replaced with the X-ray image 40. That is, in a case in which the operator inputs an index image generation command through the input device 31, the X-ray image acquisition unit 120 outputs the acquired X-ray image 40 to the index image generation unit 121, similarly to the camera image acquisition unit 80 according to the third embodiment. Similarly to the index image generation unit 115 according to the third embodiment, the index image generation unit 121 applies a known image recognition technique to the X-ray image 40 to extract the contour of the subject H included in the X-ray image 40. Then, the index image generation unit 121 generates a positioning index image 90G2 (not illustrated, which is represented by 90G2 for convenience in order to distinguish the positioning index image 90G2 from the positioning index image 90G1 according to the third embodiment) on the basis of the extracted contour.

In a case in which the positioning index image 90G2 is input from the index image generation unit 121, the index image acquisition unit 82 replaces the positioning index image 90 registered in the index image DB 76 with the positioning index image 90G2 generated by the index image generation unit 121.

Similarly to the third embodiment, it is possible to update the positioning index image 90 according to the preference of the operator or rules in medical facilities. In addition, it is possible to effectively use the X-ray image 40.

In this case, similarly to the third embodiment, the index image generation unit 121 may extract the contour from the X-ray image 40 and generate the positioning index image 90G2 whenever the positioning index image 90 is used. However, it is preferable to generate the positioning index image 90G2 only once and to store the generated positioning index image 90G2.

The X-ray image 40 which is the basis of the positioning index image 90G2 is not limited to the X-ray image 40 acquired in real time in a case in which the index image generation command has been input. The positioning index image 90G2 may be generated on the basis of the X-ray image 40 stored as the image file 41 in the PACS.

Fifth Embodiment

Figure 18:
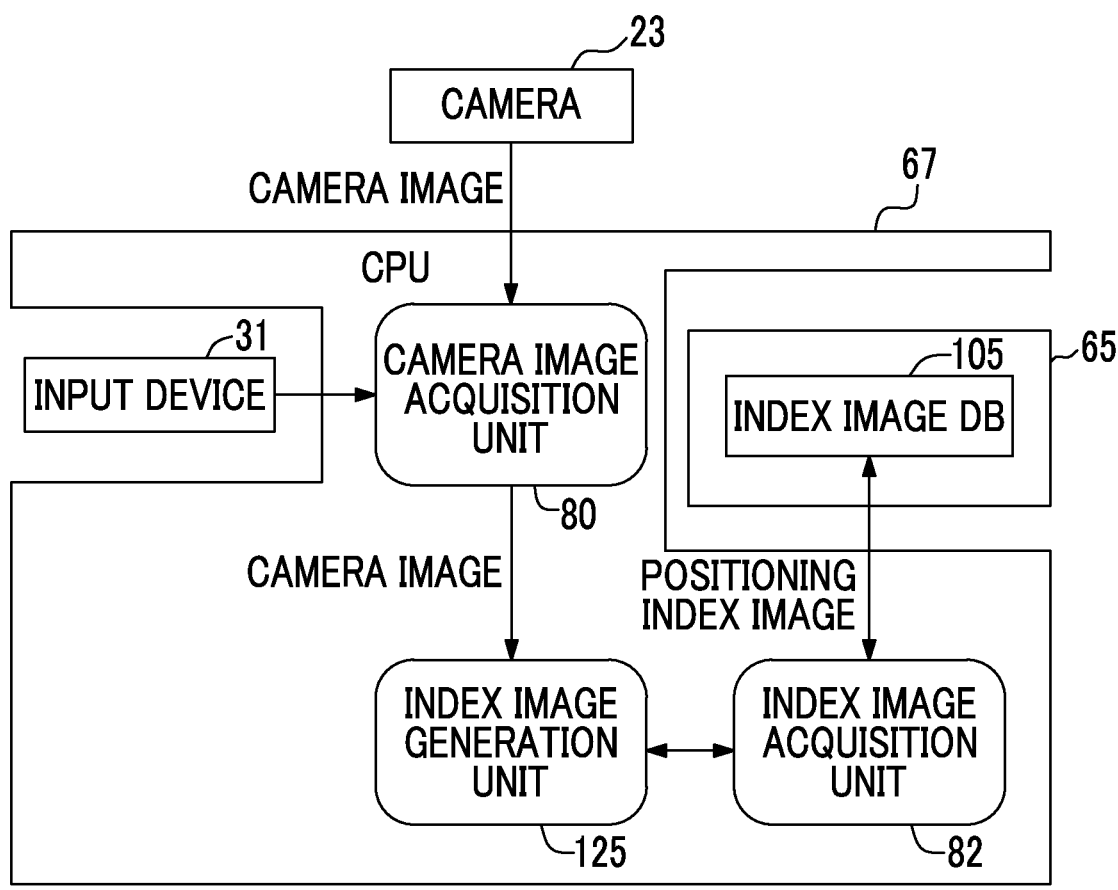
FIG. 18 is a block diagram illustrating a CPU of a console according to a fifth embodiment.
Figure 19:
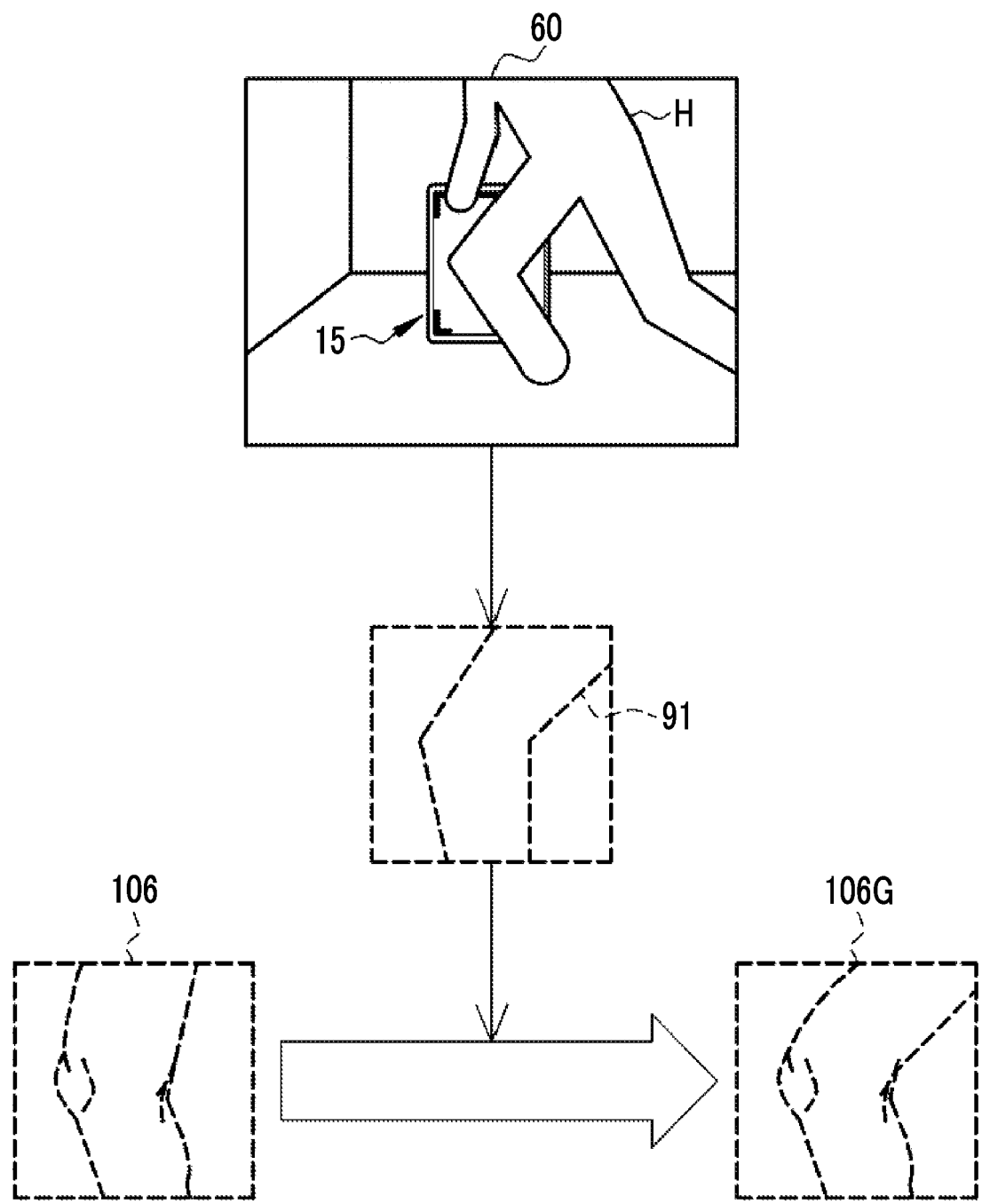
FIG. 19 is a diagram illustrating an aspect in which the posture and/or direction of a subject included in a positioning index image registered in an index image DB is edited on the basis of a camera image to generate a positioning index image.

In a fifth embodiment illustrated in FIGS. 18 to 20, in the case of the positioning index image 106 according to the second embodiment illustrated in FIG. 14, the posture and/or direction of the subject H included in a reference three-dimensional display image is edited on the basis of the camera image 60 to generate an edited three-dimensional display image and the generated edited three-dimensional display image is used as the positioning index image 106.

In FIG. 18, a CPU 67 of a console 16 according to this embodiment includes an index image generation unit 125 similarly to the third embodiment. The index image generation unit 125 edits the posture and/or direction of the subject H included in the reference three-dimensional display image on the basis of the camera image 60 to generate the edited three-dimensional display image and uses the generated edited three-dimensional display image as the positioning index image 106.

In a case in which the operator inputs an index image generation command through the input device 31, the camera image acquisition unit 80 outputs the acquired camera image 60 to the index image generation unit 125 similarly to the third embodiment. The index image acquisition unit 82 outputs the positioning index image 106 registered in the index image DB 105 to the index image generation unit 125. Here, the positioning index image 106 registered in the index image DB 105 corresponds to the reference three-dimensional display image.

As illustrated in FIG. 19, the index image generation unit 125 extracts the contour of the subject H from the camera image 60. Then, the index image generation unit 125 vectorizes the image of the extracted contour and compares the contour with the posture and direction of the subject H included in the positioning index image 106 from the index image acquisition unit 82 which is the reference three-dimensional display image. In a case in which the comparison result shows that the contour is different from the posture and/or direction of the subject H included in the positioning index image 106, the posture and/or direction of the subject included in the positioning index image 106 is edited according to the contour to generate a positioning index image 106G. The positioning index image 106G corresponds to the edited three-dimensional display image. The index image generation unit 125 outputs the positioning index image 106G to the index image acquisition unit 82. FIG. 19 illustrates the positioning index image 106G edited such that the bending angle of the upper leg with respect to the lower leg is less than that in the positioning index image 106.

In a case in which the positioning index image 106G is input from the index image generation unit 125 as illustrated in (A) of FIG. 20, the index image acquisition unit 82 replaces the positioning index image 106 registered in the index image DB 105 with the positioning index image 106G generated by the index image generation unit 125 as illustrated in (B) of FIG. 20. FIG. 20 illustrates an aspect in which the positioning index image 106 is replaced with the positioning index image 106G edited such that the bending angle of the upper leg with respect to the lower leg is less than that in the positioning index image 106 as in FIG. 19.

As such, the index image generation unit 125 edits the posture and/or direction of the subject H included in the positioning index image 106 of the index image DB 105 which is the reference three-dimensional display image on the basis of the camera image 60 to generate the edited three-dimensional display image and uses the edited three-dimensional display image as the positioning index image 106G. Therefore, similarly to the third and fourth embodiments, it is possible to update the positioning index image 106 according to the preference of the operator or rules in medical facilities. In addition, it is possible to effectively use the camera image 60.

In this case, similarly to the third and fourth embodiments, the index image generation unit 125 may generate the positioning index image 106G whenever the positioning index image 106 is used. However, it is preferable to generate the positioning index image 106G only once as described above and to store the generated positioning index image 106G.

The camera image 60 which is the basis of the positioning index image 106G may be the camera image 60 acquired by the camera image acquisition unit 80 at the time when the emission of X-rays starts, similarly to the third embodiment, or may be the camera image 60 corresponding to one frame which is selected by the operator after a motion picture of the camera images 60 is reviewed by the operator.

Sixth Embodiment

Figure 22:
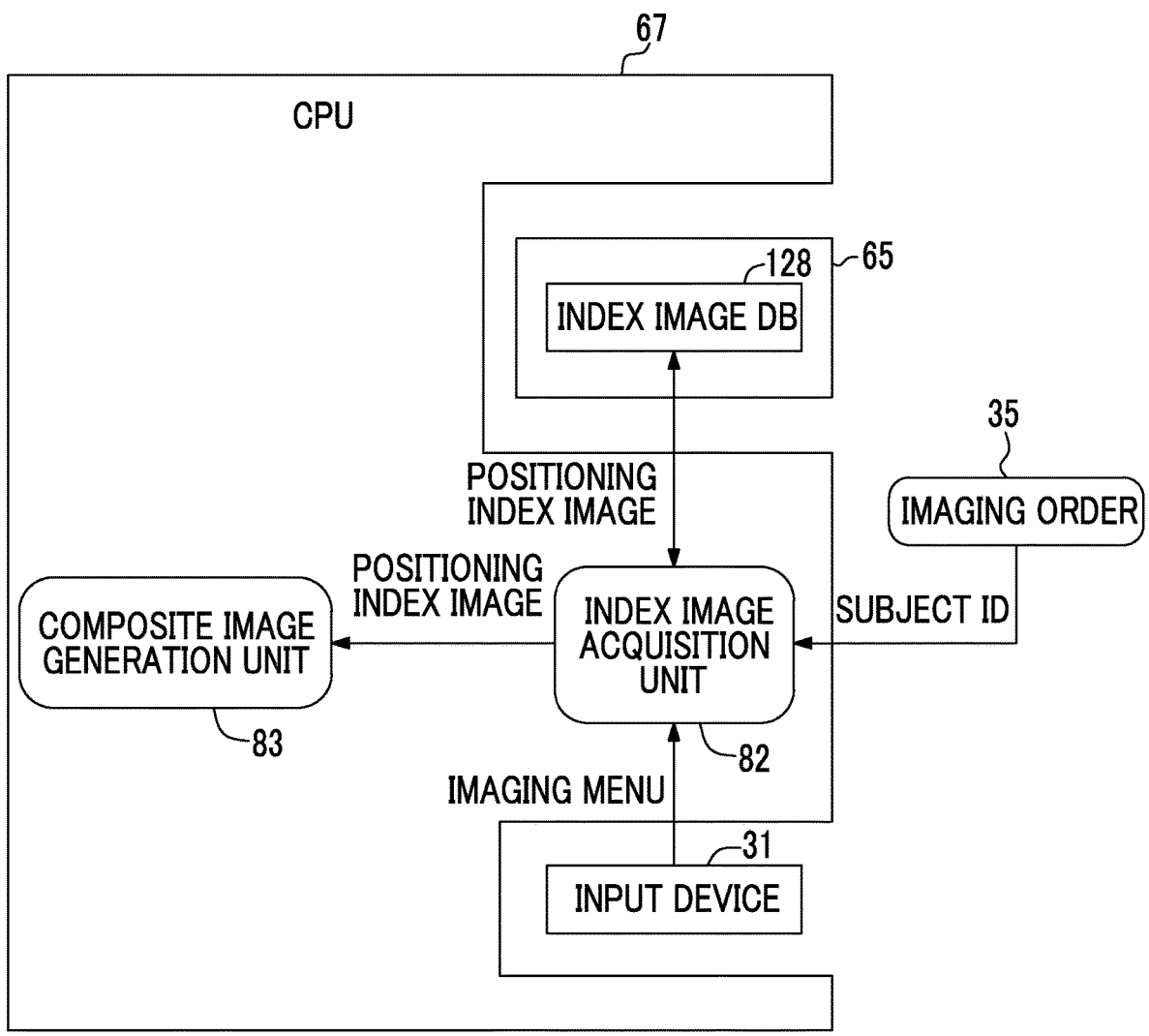
FIG. 22 is a block diagram illustrating a CPU of a console according to the sixth embodiment.

In a sixth embodiment illustrated in FIGS. 21 and 22, the positioning index image 90 is registered for each subject H.

In FIG. 21, in an index image DB 128 according to this embodiment, the positioning index image 90 is registered for each subject H and each imaging menu. In this case, as illustrated in FIG. 22, the index image acquisition unit 82 acquires the positioning index image 90 corresponding to the subject ID included in the imaging order 35 from the index image DB 128, in addition to the imaging menu input through the input device 31. For example, in a case in which the imaging menu is knee/flexed position/side and the subject ID included in the imaging order 35 is H0800, the index image acquisition unit 82 acquires the positioning index image 90 which is surrounded by a thick frame in FIG. 21 and corresponds to the subject ID "H0800", the index image ID "II0025", and the imaging menu "knee/flexed position/side".

As such, the index image acquisition unit 82 acquires the positioning index image 90 corresponding to the subject H from the index image DB 128 in which the positioning index image 90 is registered for each subject H. Therefore, it is possible to perform positioning, using the positioning index image 90 most suitable for each subject H.

The positioning index image 90 registered for each subject H in the index image DB 128 is the positioning index image 90G1 generated on the basis of the camera image 60 by the index image generation unit 115 according to the third embodiment and the positioning index image 90G2 generated on the basis of the X-ray image 40 by the index image generation unit 121 according to the fourth embodiment.

Alternatively, in the index image DB 128, the positioning index image 106G generated on the basis of the camera image 60 by the index image generation unit 125 according to the fifth embodiment may be registered for each subject H.

Seventh Embodiment

Figure 24:
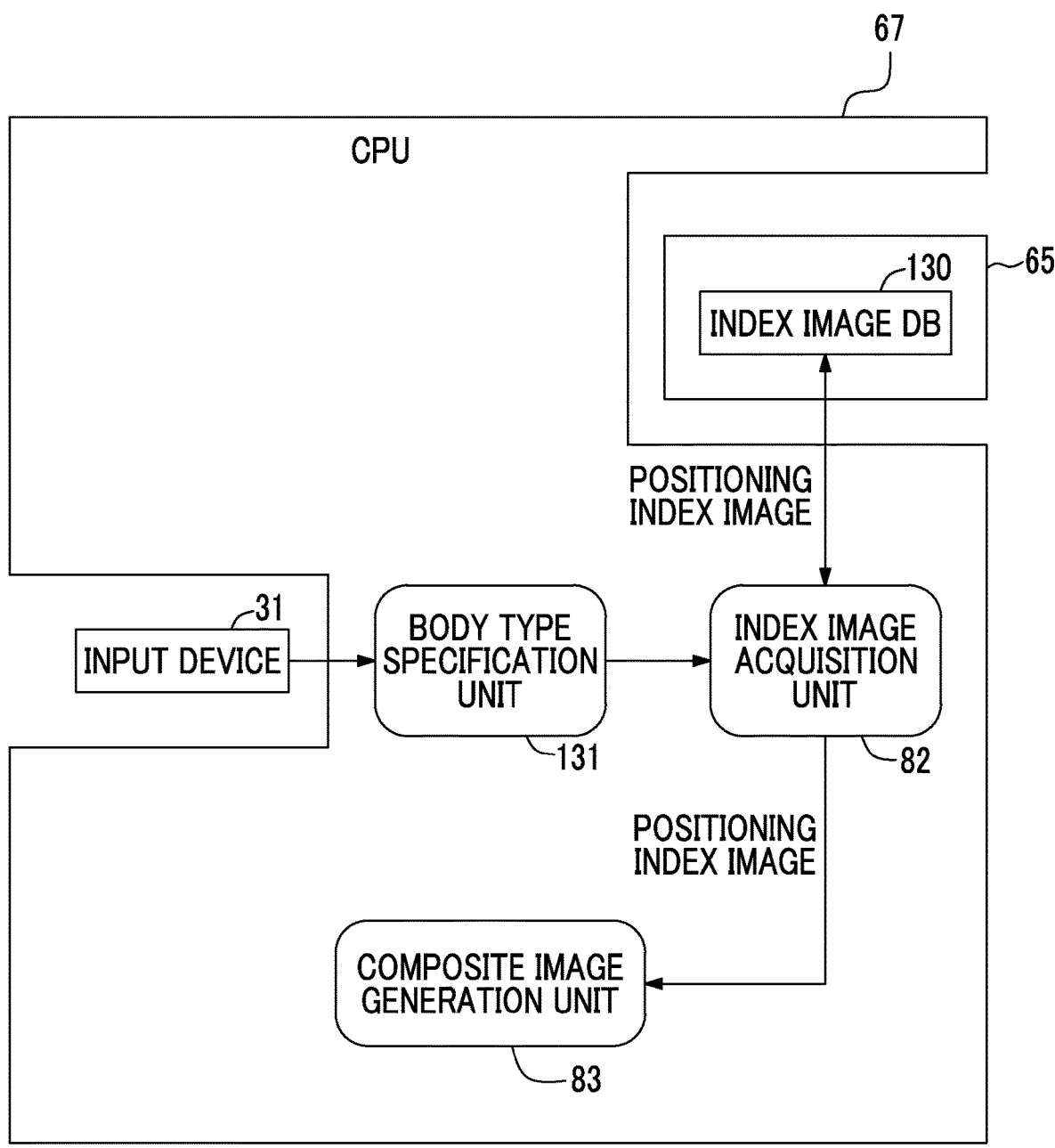
FIG. 24 is a block diagram illustrating a CPU of a console according to a seventh embodiment.

In a seventh embodiment illustrated in FIGS. 23 and 24, the positioning index image 90 is registered for each body type of the subject H.

In FIG. 23, in an index image DB 130 according to this embodiment, the positioning index image 90 is registered for each body type of the subject H and each imaging menu. There are three body types, that is, a thin body type, a normal body type, and a fat body type. In a positioning index image 90S for the thin body type, the width of the contour 91 is less than that in the positioning index image 90N for the normal body type. On the contrary, in a positioning index image 90O for the fat body type, the width of the contour 91 is greater than that in the positioning index image 90N for the normal body type.

In FIG. 24, a CPU 67 of a console 16 according to this embodiment includes a body type specification unit 131. The body type specification unit 131 receives the body type of the subject H input by the operator through the input device 31. Then, the body type specification unit 131 specifies the body type of the subject H. The body type specification unit 131 outputs the specified body type of the subject H to the index image acquisition unit 82.

The index image acquisition unit 82 acquires the positioning index image 90 corresponding to the body type of the subject H specified by the body type specification unit 131 from the index image DB 130 in addition to the imaging menu input through the input device 31. For example, in a case in which the imaging menu is knee/flexed position/side and the body type of the subject H specified by the body type specification unit 131 is the fat body type, the index image acquisition unit 82 acquires a positioning index image 90O which is surrounded by a thick frame in FIG. 23 and corresponds to an index image ID "II0020-O", the imaging menu "knee/flexed position/side", and the fat body type.

As such, the index image acquisition unit 82 acquires the positioning index image 90 corresponding to the body type of the subject H from the index image DB 130 in which the positioning index image 90 is registered for each body type of the subject H. Therefore, it is possible to perform positioning, using the positioning index image 90 most suitable for each body type of the subject H.

A method for specifying the body type of the subject H is not limited to the method in which the operator inputs the body type of the subject H through the input device 31. The contour of the subject H may be extracted from the camera image 60 and the extracted contour may be collated with the contour of each body type which has been registered in advance to specify the body type of the subject H. In this case, the camera image acquisition unit 80 outputs the camera image 60 to the body type specification unit 131. Alternatively, a body mass index (BMI) may be calculated from a height and a weight in subject information included in the imaging order 35 and the body type of the subject H may be specified on the basis of the BMI.

The body types of the subject H are not limited to the thin body type, the normal body type, and the fat body type. The body types may include, for example, a large body type and a small body type.

The positioning index image 90 may not be registered for each body type of the subject H, but one type of positioning index image 90 may be provided and changed depending on the body type of the subject H. In this case, it is necessary to change the positioning index image 90 depending on the body type of the subject H whenever the positioning index image 90 is used, which requires a lot of time and effort. Therefore, it is preferable to register the positioning index image 90 for each body type of the subject H as illustrated in FIG. 23.

The positioning index image 106 according to the second embodiment may be used instead of the positioning index image 90. This holds for the following eighth to eleventh embodiments.

Eighth Embodiment

Figure 25:
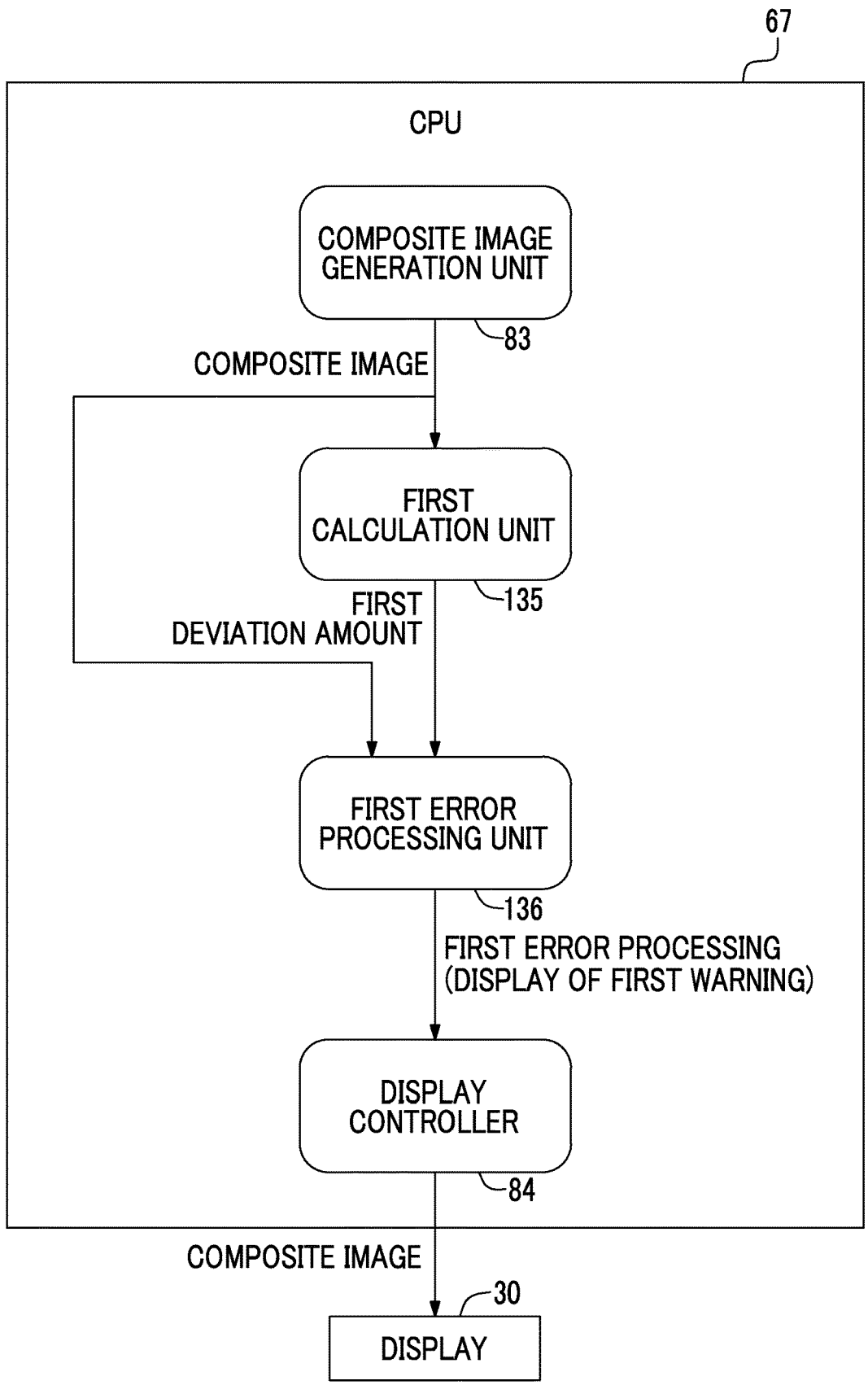
FIG. 25 is a block diagram illustrating a CPU of a console according to an eighth embodiment.
Figure 26:
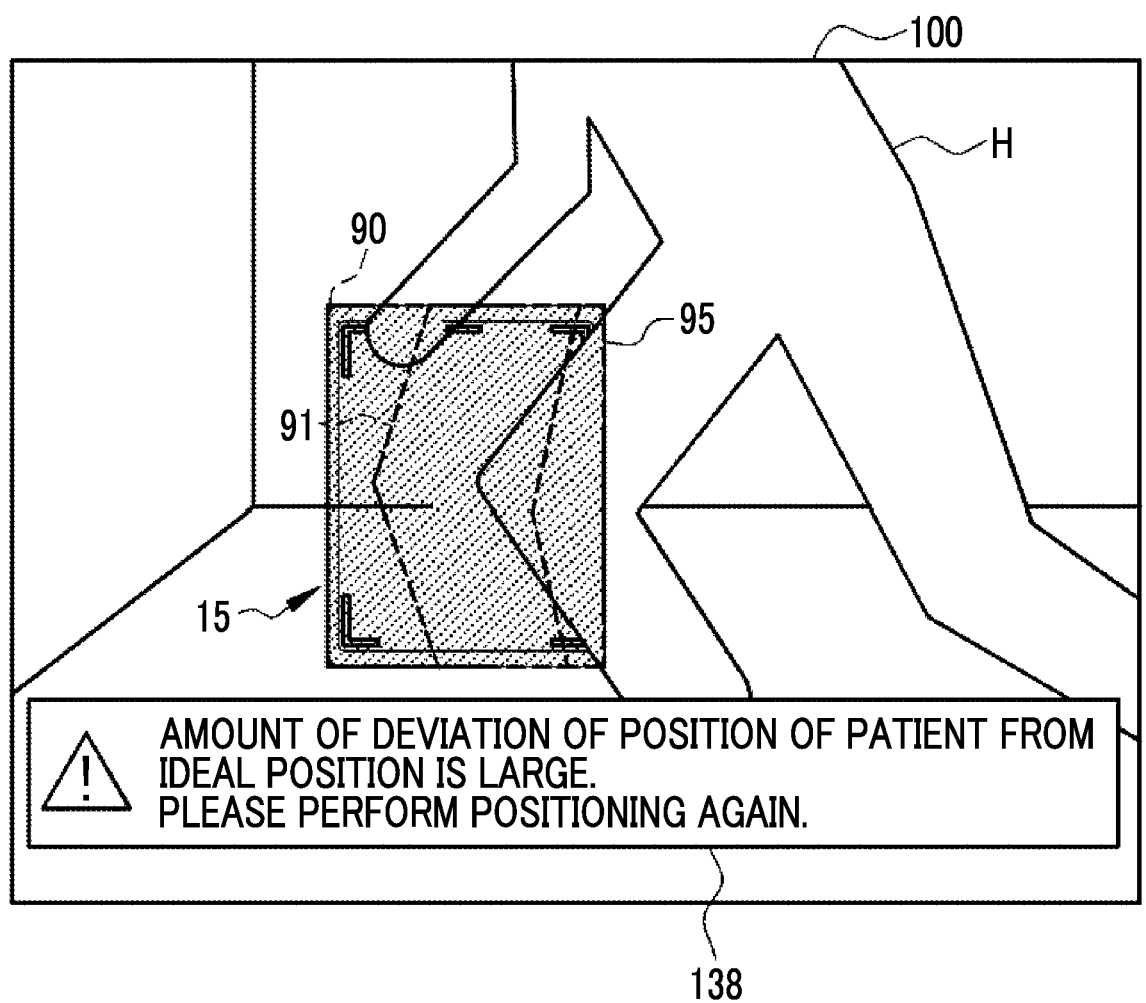
FIG. 26 is a diagram illustrating a composite image in which a first warning is displayed.

In an eighth embodiment illustrated in FIGS. 25 and 26, a first deviation amount which is the amount of deviation between the set position indicated by the positioning index image 90 and the actual position of the subject H is calculated and first error processing is performed in a case in which the first deviation amount is greater than a predetermined first threshold value.

In FIG. 25, a CPU 67 of a console 16 according to this embodiment includes a first calculation unit 135 and a first error processing unit 136.

In this case, the composite image generation unit 83 outputs the composite image 100 to the first calculation unit 135 and the first error processing unit 136. The first calculation unit 135 calculates the first deviation amount which is the amount of deviation between the set position indicated by the positioning index image 90 and the actual position of the subject H on the basis of the composite image 100 from the composite image generation unit 83. The first calculation unit 135 extracts the contour of the subject H included in the composite image 100 using a known image recognition technique. Then, the first calculation unit 135 extracts the contour of the imaging part set in the imaging menu from the extracted contour. The first calculation unit 135 calculates a difference between the extracted contour of the imaging part and the contour 91 of the positioning index image 90 and outputs the difference as the first deviation amount to the first error processing unit 136.

The first error processing unit 136 performs the first error processing in a case in which the first deviation amount from the first calculation unit 135 is greater than the predetermined first threshold value. On the other hand, in a case in which the first deviation amount is equal to or less than the first threshold value, the first error processing unit 136 does not perform the first error processing.

As illustrated in FIG. 26, the first error processing unit 136 performs, as the first error processing, a process of displaying a first warning 138 on the composite image 100 from the composite image generation unit 83. The first warning 138 is a message which informs the operator that the amount of deviation of the position of the subject H from the set position is large and which prompts the operator to perform positioning again. The operator sees the first warning 138 and performs positioning again such that the position of the subject H is matched with the set position.

As such, the first deviation amount which is the amount of deviation between the set position indicated by the positioning index image 90 and the actual position of the subject H is calculated and the first error processing is performed in a case in which the first deviation amount is greater than the predetermined first threshold value. Therefore, it is possible to prevent X-ray imaging from being performed in a state in which the amount of deviation of the position of the subject H from the set position is large. As a result, it is possible to further reduce the probability that an imaging error will occur.

As the first error processing, a process of outputting warning sounds, such as beep sounds, may be performed instead of or in addition to the display of the first warning 138.

In a case in which the radiation source control device 14 and the console 16 are connected to each other and the first deviation amount is greater than the first threshold value, a process of transmitting an irradiation prohibition signal for prohibiting the emission of X-rays from the console 16 to the radiation source control device 14 may be performed as the first error processing. In this case, it is possible to certainly prevent X-ray imaging from being performed in a state in which the amount of deviation of the position of the subject H from the set position is large.

The first error processing unit 136 may perform the first error processing in a case in which the state in which the first deviation amount is greater than the first threshold value is maintained for a predetermined period of time. In this case, it is possible to prevent the first error processing from being unnecessarily performed.

Ninth Embodiment

Figure 27:
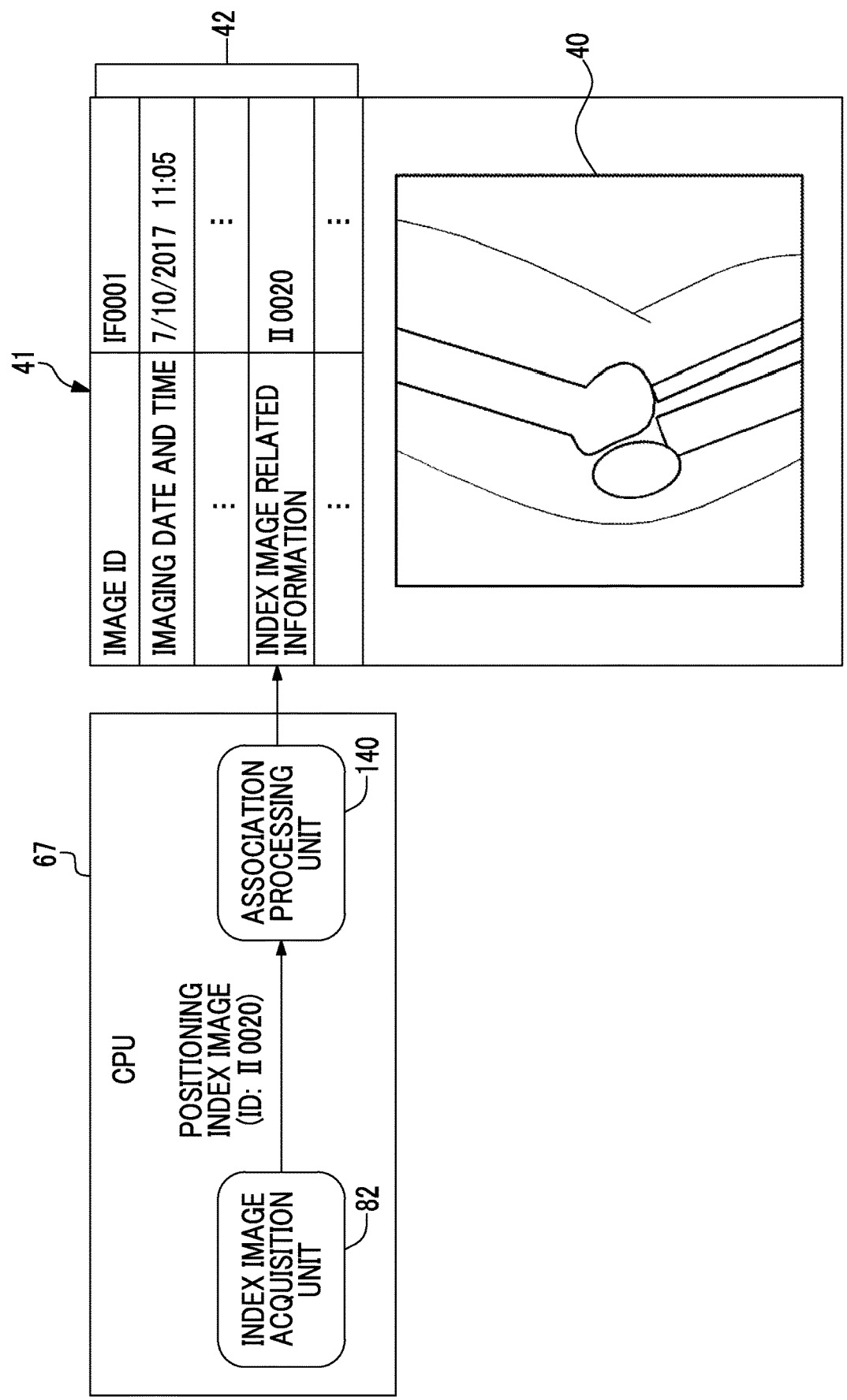
FIG. 27 is a block diagram illustrating a CPU of a console according to a ninth embodiment.

In a ninth embodiment illustrated in FIG. 27, related information of the positioning index image 90 is associated as the accessory information 42 of the X-ray image 40 with the X-ray image 40.

In FIG. 27, a CPU 67 of a console 16 according to this embodiment includes an association processing unit 140.

The index image acquisition unit 82 outputs the same positioning index image 90 as that output to the composite image generation unit 83 to the association processing unit 140. The association processing unit 140 inserts the index image ID of the positioning index image 90 from the index image acquisition unit 82 as the related information (hereinafter, referred to index image related information) of the positioning index image 90 into the accessory information 42 of the image file 41.

As such, since the index image related information is associated as the accessory information 42 with the X-ray image 40, it is possible to immediately know which positioning index image 90 has been used for X-ray imaging with reference to the accessory information 42. Therefore, for example, in a case in which the operator examines the improvement of imaging with reference to the past imaging, it is possible to make a detailed examination considering the positioning index image 90.

As the index image related information, a still image or a motion picture of the composite image 100 including the positioning index image 90 or a still image or a motion picture of an image obtained by trimming a portion including the positioning index image 90 from the composite image 100 may be used instead of or in addition to the index image ID. In the case of the still image, for example, a still image captured at the time when the emission of X-rays starts is used. In the case of the motion picture, for example, a motion picture captured for a predetermined period between the times when the emission of X-rays starts is used.

In addition, for example, only the contour 91 of the positioning index image 90 or the position coordinates of the positioning index image 90 in the composite image 100 may be associated as the index image related information. That is, any index image related information may be used as long as it indicates which positioning index image 90 has been used.

Tenth Embodiment

Figure 28:
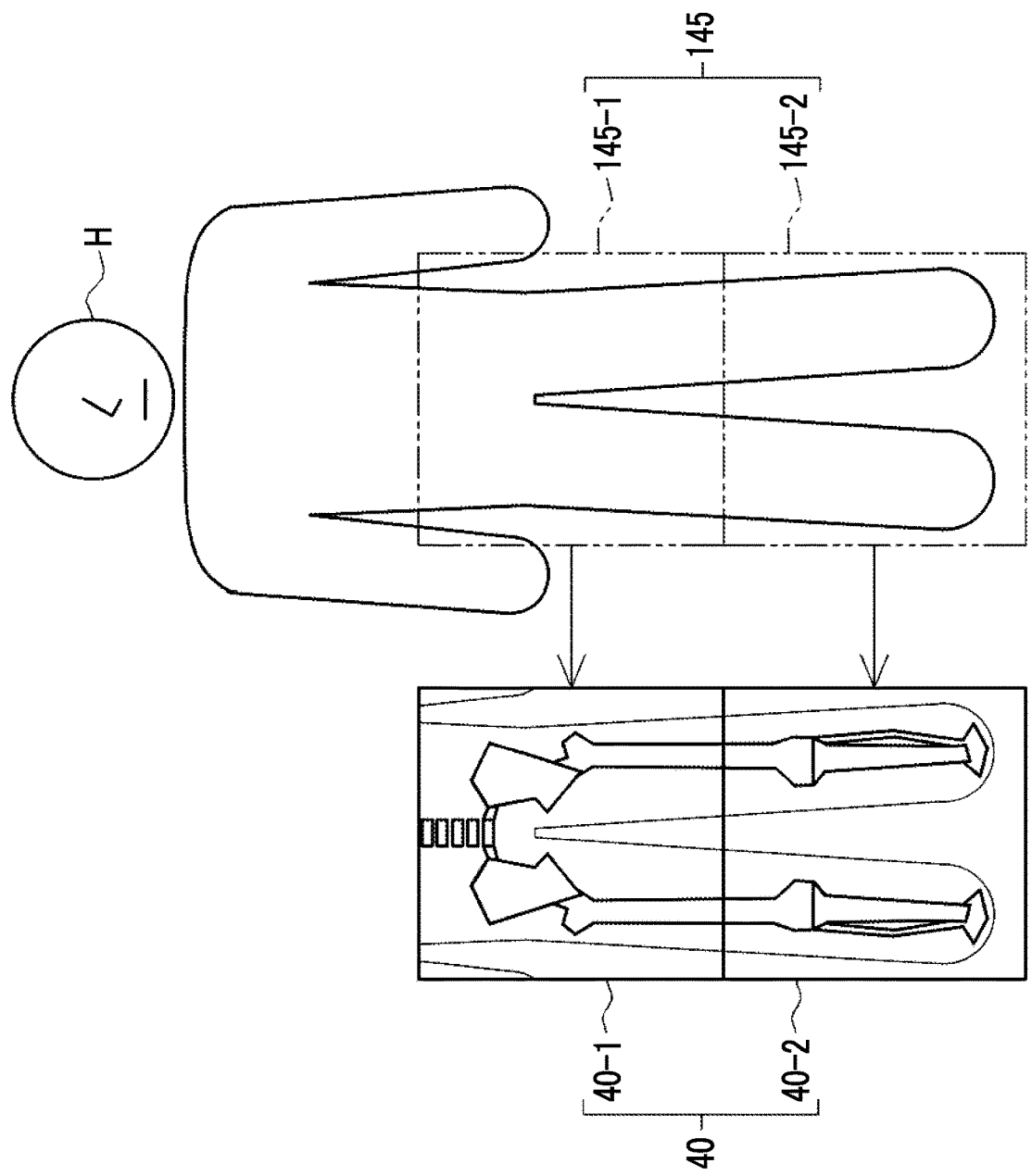
FIG. 28 is a diagram illustrating an imaging range and an X-ray image in the case of lower limb imaging.
Figure 29:
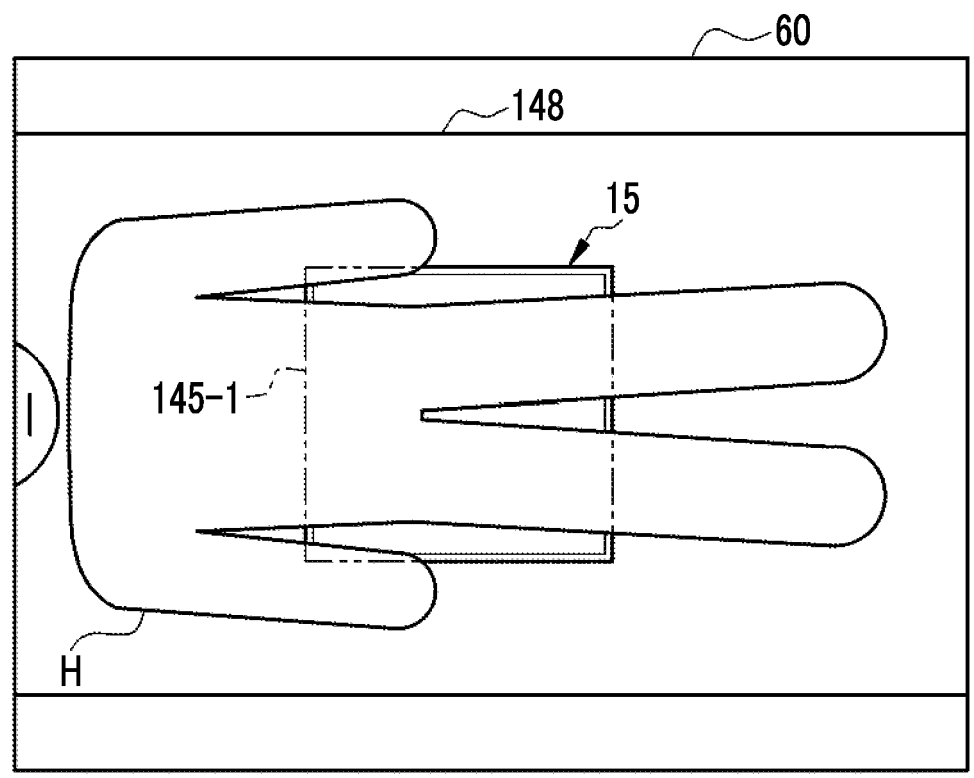
FIG. 29 is a diagram illustrating a camera image in a case in which an electronic cassette is positioned in a reference divided imaging range.
Figure 30:
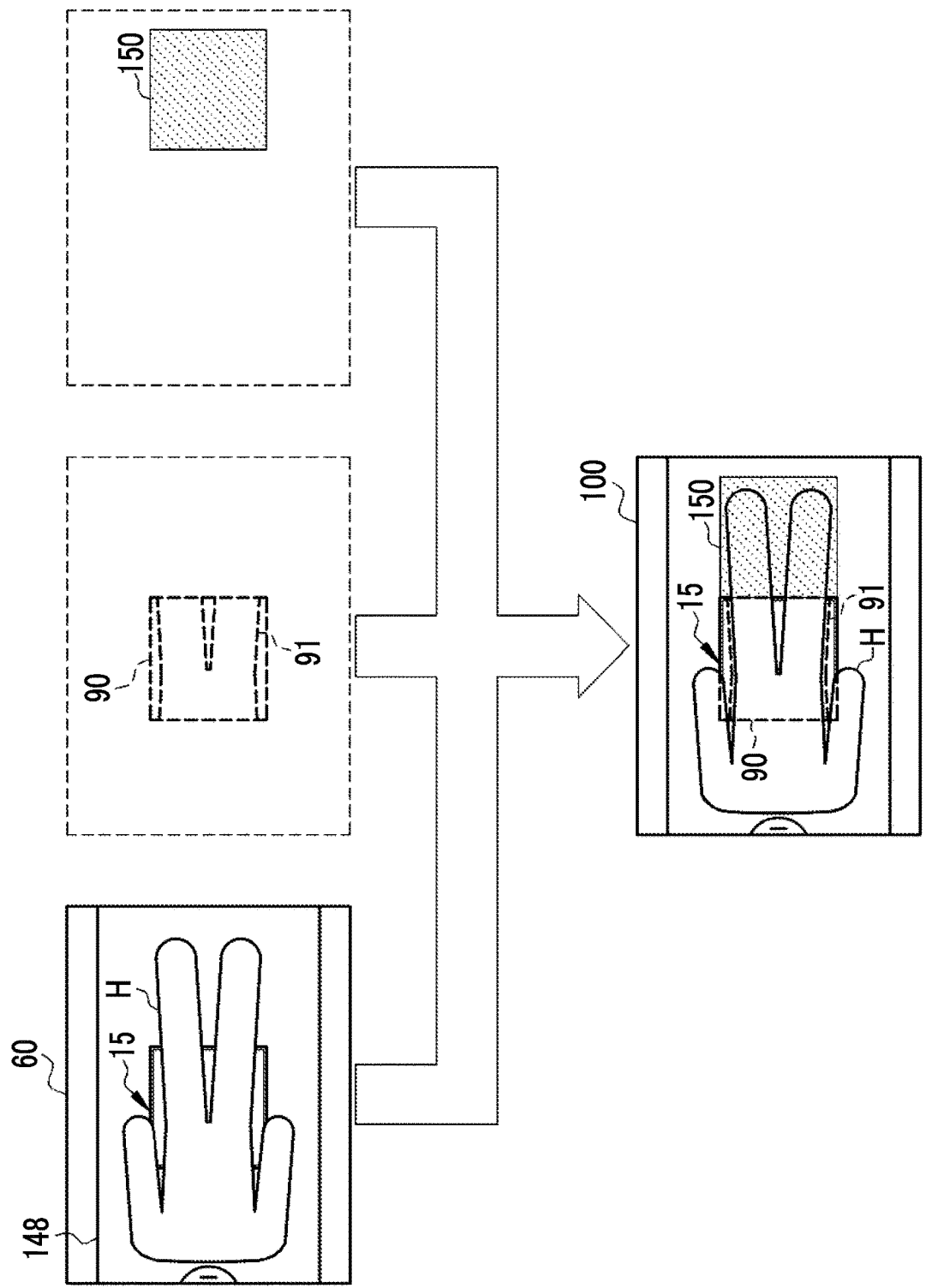
FIG. 30 is a diagram illustrating the generation of a composite image in a tenth embodiment.

A tenth embodiment illustrated in FIGS. 28 to 30 relates to long-length imaging which divides a long imaging range including a plurality of imaging parts of the subject H into a plurality of divided imaging ranges, captures the plurality of divided imaging ranges, and combines a plurality of X-ray images corresponding to each divided imaging range to generate a long X-ray image.

FIG. 28 illustrates an imaging range and an X-ray image in the case of lower limb imaging which is an example of the long-length imaging. In this case, a plurality of imaging parts of the subject H are two parts, that is, the upper leg including the waist and the lower leg. The, the imaging range 145 is divided into two portions, that is, a divided imaging range 145-1 corresponding to the upper leg including the waist and a divided imaging range 145-2 corresponding to the lower leg. The divided imaging range 145-1 corresponds to a reference divided imaging range and the divided imaging range 145-2 corresponds to the other divided imaging range. In this case, the X-ray image 40 is a composite image of two X-ray images 40-1 and 40-2 corresponding to the divided imaging ranges 145-1 and 145-2.

In the case of the long-length imaging, for example, the electronic cassettes 15 are positioned for all of the plurality of divided imaging ranges and each of the electronic cassettes 15 is irradiated with X-rays. Therefore, in one long-length imaging operation, the number of times the X-rays are emitted is equal to the number of divided imaging ranges.

FIG. 29 illustrates a camera image 60 in a case in which the electronic cassette 15 is positioned in the divided imaging range 145-1 which is the reference divided imaging range. For example, the subject H lies supine on a bed 148 in an imaging room. The detection unit 81 detects the in-image cassette position of the electronic cassette 15 positioned in the divided imaging range 145-1 from the camera image 60.

As illustrated in FIG. 30, the composite image generation unit 83 combines the camera image 60, the positioning index image 90, and a recommended cassette frame 150 as a recommended cassette position index to generate a composite image 100. The composite image generation unit 83 displays the positioning index image 90 and the recommended cassette frame 150 with respect to the in-image cassette position of the electronic cassette 15 positioned in the divided imaging range 145-1 which has been detected by the detection unit 81. The cassette frame 95 is not illustrated in FIG. 30.

The recommended cassette frame 150 indicates the recommended position of the electronic cassette 15 in the divided imaging range other than the reference divided imaging range, that is, the divided imaging range 145-2. Similarly to the cassette frame 95, the recommended cassette frame 150 has a rectangular shape simulating the outward shape of the front surface 52A and the inside of the rectangular cassette frame 150 is painted in a specific light color such that the background is transparent.

As such, in a case in which the long-length imaging is performed, the recommended cassette frame 150 indicating the recommended position of the electronic cassette 15 in the divided imaging range other than the reference divided imaging range is displayed. Therefore, the operator knows the recommended position of the electronic cassette 15 in the other divided imaging range at a glance. Therefore, it is possible to perform positioning in the long-length imaging, without any problem.

Figure 31:
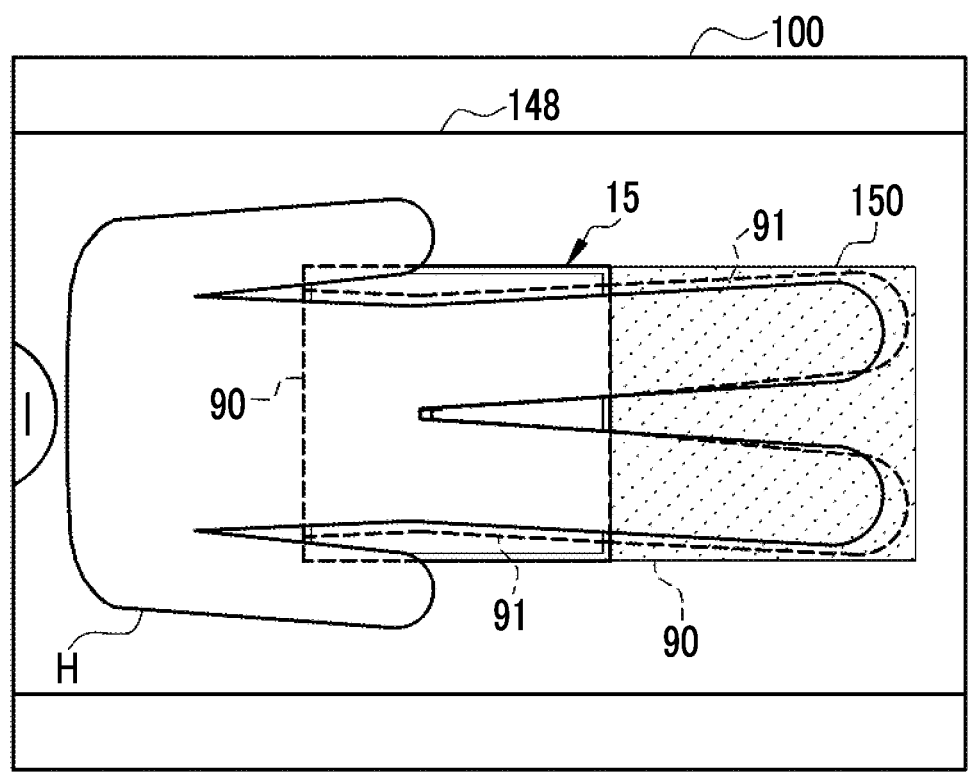
FIG. 31 is a diagram illustrating an aspect in which a positioning index image is displayed in a recommended cassette frame.

As illustrated in FIG. 31, the composite image generation unit 83 may display the positioning index image 90 on the recommended cassette frame 150. In this case, it is possible to know the set position as well as the recommended position of the electronic cassette 15 in the other divided imaging range and thus to smoothly perform positioning during long-length imaging.

Eleventh Embodiment

Figure 32:
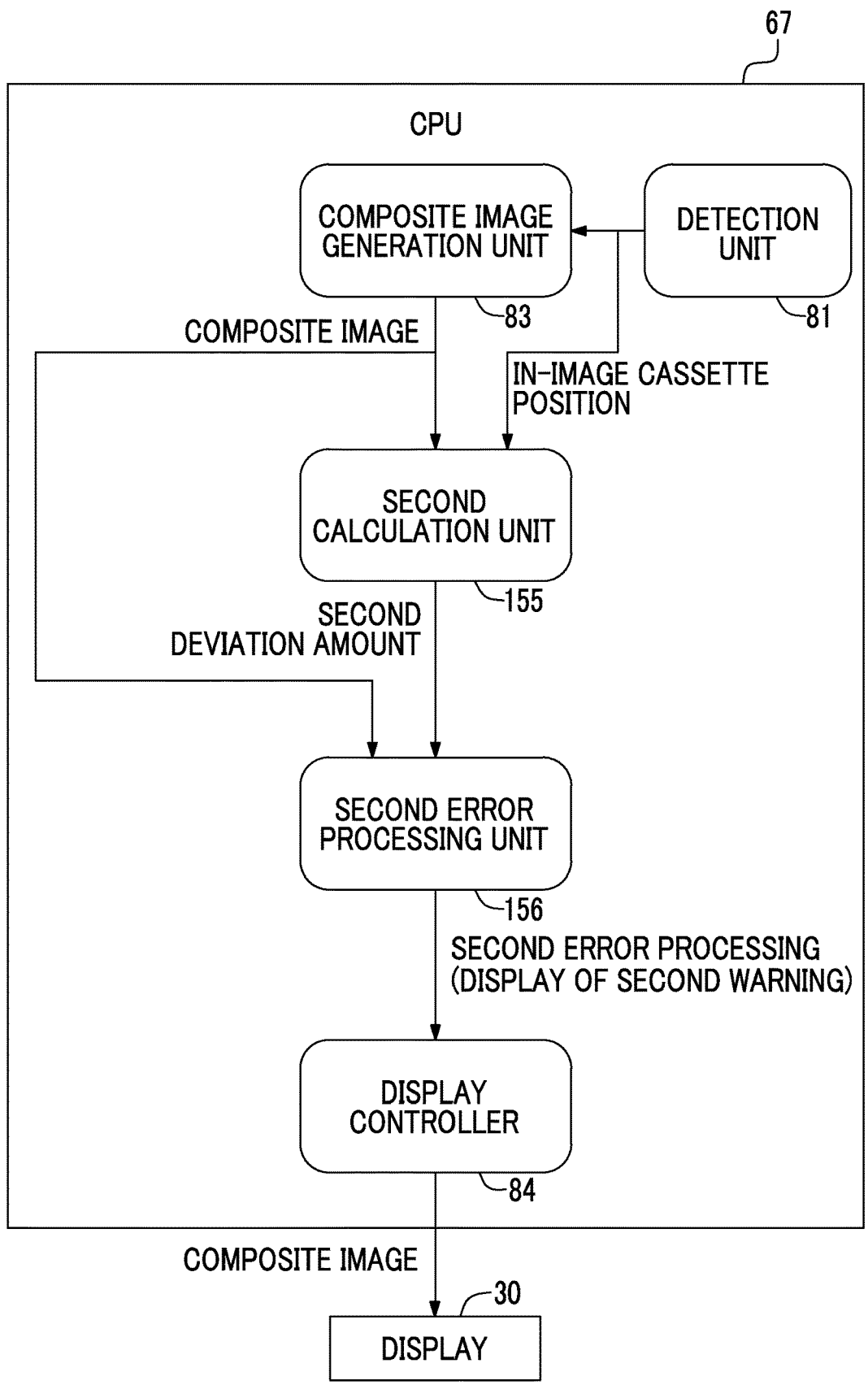
FIG. 32 is a block diagram illustrating a CPU of a console according to an eleventh embodiment.
Figure 33:
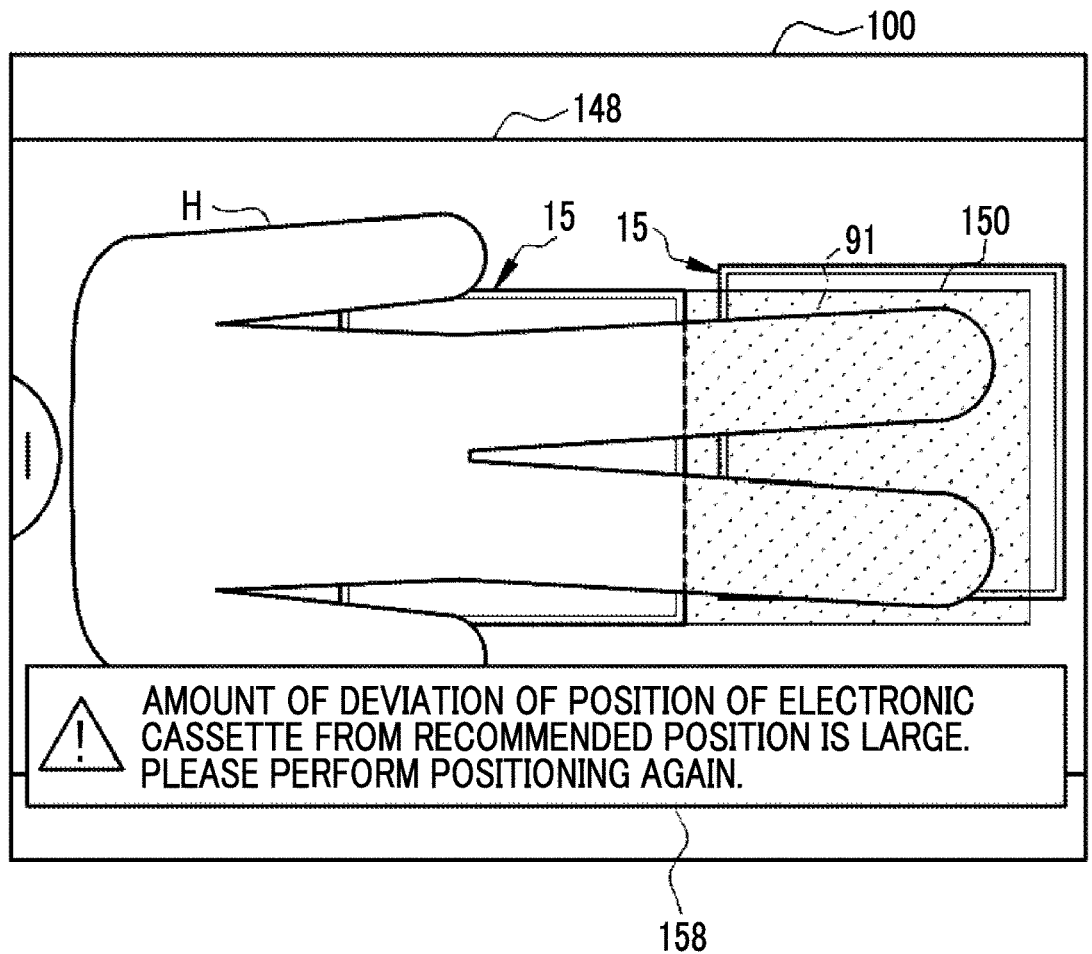
FIG. 33 is a diagram illustrating a composite image in which a second warning is displayed.

In an eleventh embodiment illustrated in FIGS. 32 and 33, a second deviation amount which is the amount of deviation between the recommended position indicated by the recommended cassette frame 150 and the actual position of the electronic cassette 15 is calculated in the case of the tenth embodiment in which the recommended cassette frame 150 is displayed and second error processing is performed in a case in which the second deviation amount is greater than a predetermined second threshold value.

In FIG. 32, a CPU 67 of a console 16 according to this embodiment includes a second calculation unit 155 and a second error processing unit 156. In this case, the detection unit 81 outputs the in-image cassette position to both the composite image generation unit 83 and the second calculation unit 155. In addition, the composite image generation unit 83 outputs the composite image 100 to the second calculation unit 155 and the second error processing unit 156.

The second calculation unit 155 calculates the second deviation amount which is the amount of deviation between the recommended position of the electronic cassette 15 indicated by the recommended cassette frame 150 and the actual position of the electronic cassette 15. The second calculation unit 155 calculates a difference between the recommended cassette frame 150 displayed in the composite image 100 from the composite image generation unit 83 and the in-image cassette position, that is, the actual position of the electronic cassette 15 from the detection unit 81 and outputs the difference as the second deviation amount to the second error processing unit 156.

The second error processing unit 156 performs the second error processing in a case in which the second deviation amount from the second calculation unit 155 is greater than the predetermined second threshold value. On the other hand, in a case in which the second deviation amount is equal to or less than the second threshold value, the second error processing unit 156 does not perform the second error processing.

As illustrated in FIG. 33, the second error processing unit 156 performs, as the second error processing, a process of displaying a second warning 158 on the composite image 100 from the composite image generation unit 83. The second warning 158 is a message which informs the operator that the amount of deviation of the position of the electronic cassette 15 from the recommended position is large and which prompts the operator to perform positioning again. The operator sees the second warning 158 and performs positioning again such that the position of the electronic cassette 15 is matched with the recommended position.

As such, the second deviation amount which is the amount of deviation between the recommended position of the electronic cassette 15 indicated by the recommended cassette frame 150 and the actual position of the electronic cassette 15 is calculated and the second error processing is performed in a case in which the second deviation amount is greater than the predetermined second threshold value. Therefore, it is possible to prevent X-ray imaging from being performed in a state in which the amount of deviation of the position of the electronic cassette 15 from the recommended position is large. As a result, it is possible to further reduce the probability that an imaging error will occur.

As the second error processing, a process of outputting warning sounds, such as beep sounds, may be performed instead of or in addition to the display of the second warning 158, similarly to the first error processing according to the eighth embodiment.

In a case in which the radiation source control device 14 and the console 16 are connected to each other and the second deviation amount is greater than the second threshold value, a process of transmitting an irradiation prohibition signal for prohibiting the emission of X-rays from the console 16 to the radiation source control device 14 may be performed as the second error processing. In this case, it is possible to certainly prevent X-ray imaging from being performed in a state in which the amount of deviation of the position of the electronic cassette 15 from the recommended position is large.

The second error processing unit 156 may perform the second error processing in a case in which the state in which the second deviation amount is greater than the second threshold value is maintained for a predetermined period of time. In this case, it is possible to prevent the second error processing from being unnecessarily performed.

In the tenth and eleventh embodiments, lower limb imaging has been described as the long-length imaging. However, full spine imaging that covers the upper half of the body of the subject from the head to the waist may be performed. In addition, two or more divided imaging ranges maybe provided.

Twelfth Embodiment

Figure 34:
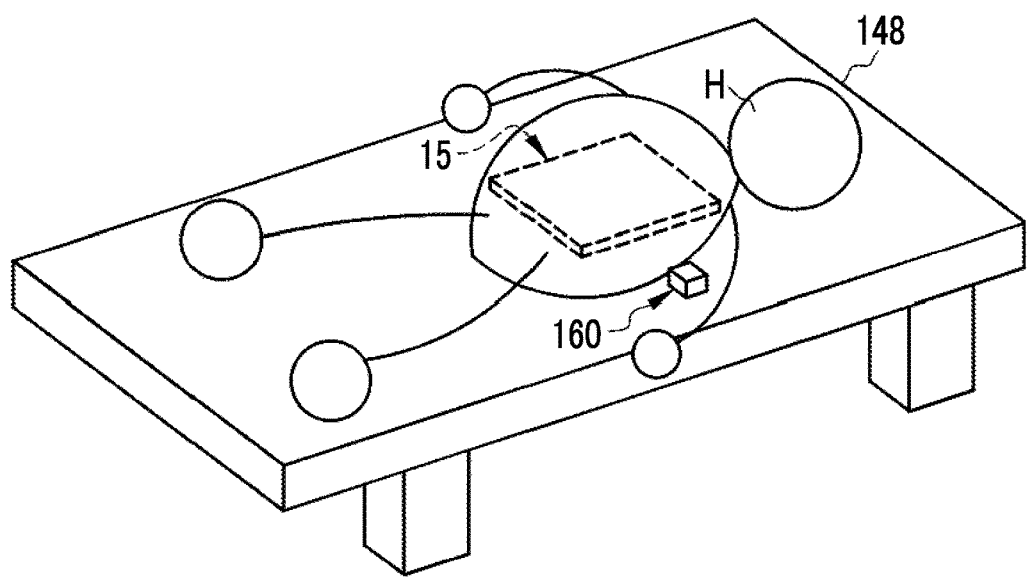
FIG. 34 is a diagram illustrating a position detection unit provided at an exposure position.
Figure 35:
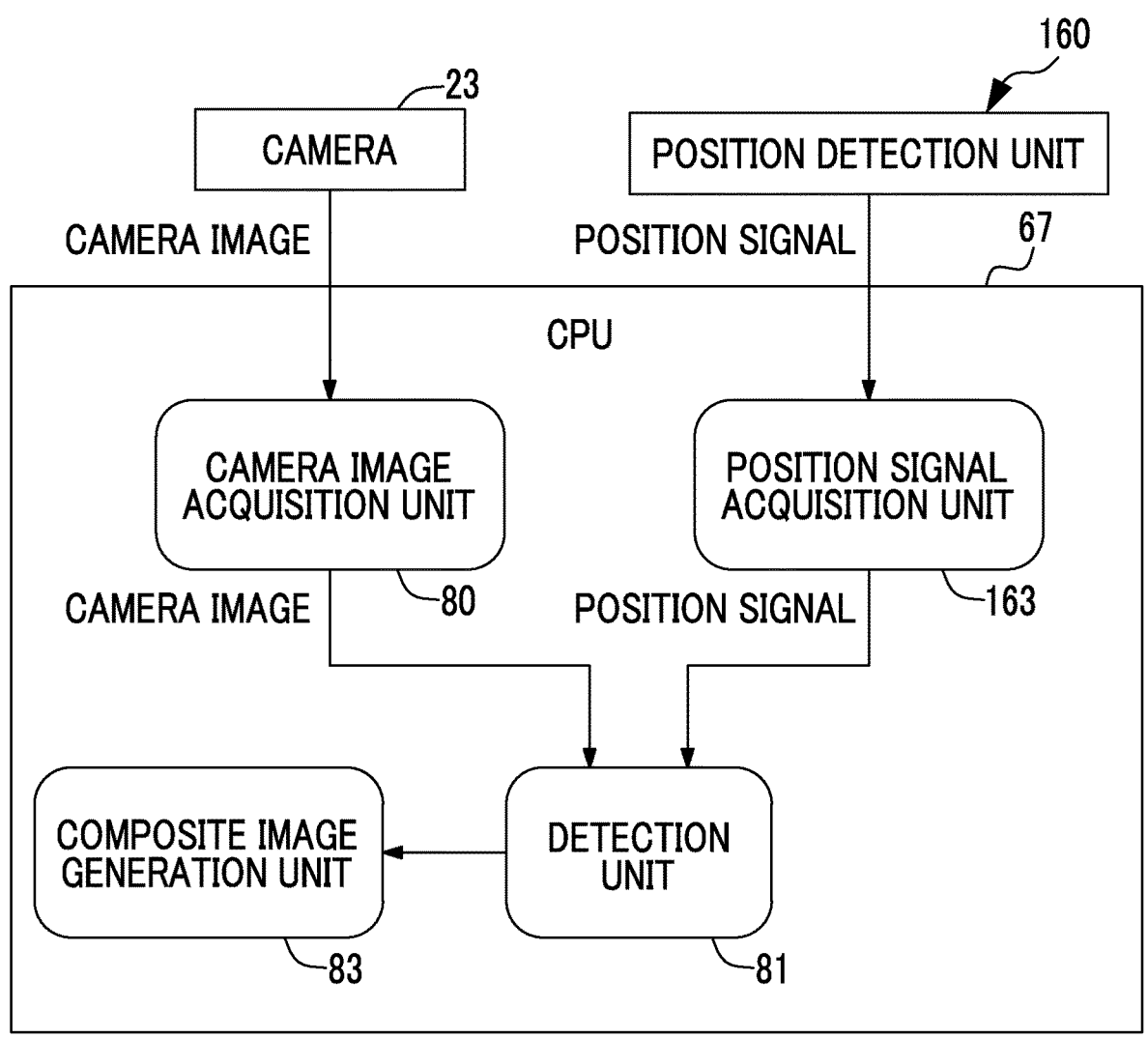
FIG. 35 is a block diagram illustrating a CPU of a console according to a twelfth embodiment.

A twelfth embodiment illustrated in FIGS. 34 and 35 relates to a method for detecting the in-image cassette position in a case in which the electronic cassette 15 is covered by the subject H.

For example, as illustrated in FIG. 29, in free imaging, in some cases, most of the electronic cassette 15 is covered by the subject H. In this case, it is difficult for the detection unit 81 to specify the characteristics of the electronic cassette 15 from the camera image 60 and to detect the in-image cassette position.

For this reason, in this embodiment, a position detection unit 160 is used as illustrated in FIG. 34. The position detection unit 160 is provided at an exposure position of the camera image 60 in the FOV of the camera 23. The position detection unit 160 outputs a position signal indicating the position of a part of a peripheral portion of the electronic cassette 15.

The position detection unit 160 includes an image sensor that outputs, as the position signal, a two-dimensional image of the position of a part of the peripheral portion of the electronic cassette 15, for example, the position of the side of the electronic cassette 15 in a space between the subject H and the bed 148. The image sensor is any one of an optical camera, a time-of-flight camera, an ultrasound sensor, and a radar sensor.

Alternatively, the position detection unit 160 includes an electromagnetic wave generation source that generates electromagnetic waves and electromagnetic wave detection sensors that are attached to parts of the peripheral portion of the electronic cassette 15, for example, four corners of the front surface 52A and detect the electromagnetic waves. In this case, the electromagnetic wave generation source is disposed at the exposure position. The electromagnetic wave generation source is a magnetic field generation source or an electric field generation source and the electromagnetic wave detection sensor is a magnetic detection sensor or a radio wave detection sensor.

In FIG. 35, a CPU 67 of a console 16 according to this embodiment includes a position signal acquisition unit 163. The position signal acquisition unit 163 acquires the position signal from the position detection unit 160 and outputs the position signal to the detection unit 81.

In this case, the detection unit 81 calculates the positions of four corners of the front surface 52A as the in-image cassette position on the basis of the position signal and the position, direction, and size of the position detection unit 160 included in the camera image 60. Specifically, the detection unit 81 calculates a coordinate transformation matrix for converting a unit coordinate system which is a coordinate system of the position detection unit 160 into a camera coordinate system which is a coordinate system of the camera 23 from the position, direction, and size of the position detection unit 160 included in the camera image 60 and calculates the coordinates of the positions of the four corners of the front surface 52A represented by the camera coordinate system from the coordinate transformation matrix and the coordinates of the positions of the four corners of the front surface 52A represented by the unit coordinate system.

As such, even in a case in which the electronic cassette 15 is covered by the subject H, it is possible to calculate the in-image cassette position using the position detection unit 160.

Image recognition may be performed for an imaging part of the subject H from the camera image 60 and the imaging menus related to the image-recognized imaging part may be displayed on the display 30 such that they can be set and the operator selects a desired imaging menu. For example, in a case in which the chest of the subject H is included in the camera image 60 and the imaging part is recognized as the chest by image recognition, the imaging menus related to the chest, such as an imaging menu "chest/decubitus position/front" an imaging menu "chest/decubitus position/rear", and an imaging menu "chest/upright position/front", are displayed on the display 30 such that they can be set.

The cassette position index indicating the position of the electronic cassette 15 is not limited to the cassette frame 95 having a rectangular shape simulating the outward shape of the front surface 52A. The cassette position index may be a cassette frame in which four corners of the front surface 52A are represented by L-shaped lines. This holds for the recommended cassette frame 150.

In some of the imaging menus, a relatively large number of imaging errors occur for the reason that it is difficult to perform positioning, the frequency of imaging is low, and the operator does not learn the imaging menus. Therefore, the imaging menu in which a relatively large number of imaging errors occur is registered as a menu in which an imaging error occurs frequently in the menu-condition table 38 in advance. In a case in which the menu in which an imaging error occurs frequently is set, it is preferable that a message indicating that a large number of errors are likely to occur during imaging corresponding to the imaging menu is displayed on the display 30 to inform the operator that imaging errors are likely to occur frequently.

For some subjects H, it is difficult to position the subject H since the subject H has difficulty in bending the joints due to, for example, disease or aging, which results in a relatively large number of imaging errors. Therefore, the subject H causing a relatively large number of imaging errors is registered as a subject H who frequently causes imaging errors in advance. In a case in which imaging is performed for the subject H who frequently causes imaging errors, it is preferable that a message indicating that the subject H is likely to cause a large number of errors during imaging is displayed on the display 30 to inform the operator that the subject H is likely to cause a large number of errors.

The display unit that displays the composite image 100 is not limited to the display 30 of the console 16 described in each of the above-mentioned embodiments. For example, the composite image 100 may be displayed on a tablet terminal carried by the operator OP. In a case in which the subject H moves, the tablet terminal may be placed at a position where the subject H can see images such that the subject H also sees the composite image 100 to cooperate in positioning.

In each of the above-described embodiments, for example, the hardware structures of the processing units performing various processes, such as the camera image acquisition unit 80, the detection unit 81, the index image acquisition unit 82, the composite image generation unit 83, the display controller 84, the index image generation units 115, 121, and 125, the X-ray image acquisition unit 120, the body type specification unit 131, the first calculation unit 135, the first error processing unit 136, the association processing unit 140, the second calculation unit 155, and the second error processing unit 156, are the following various processors.

Various processors include, for example, a CPU, a programmable logic device (PLD), and a dedicated electric circuit. The CPU is a general-purpose processor that executes software (program) to function as various processing units as it is known. The PLD is a processor whose circuit configuration can be changed after it is manufactured, such as a field programmable gate array (FPGA). The dedicated electric circuit is a processor having a dedicated circuit configuration designed to perform a specific process, such as an application specific integrated circuit (ASIC).

One processing unit may be one of the various processors or a combination of two or more processors of the same type or different types (for example, a combination of a plurality of FPGAs and a combination of a CPU and an FPGA). In addition, a plurality of processing units may be formed by one processor. As an example in which a plurality of processing units are formed by one processor, first, one processor is formed by a combination of one or more CPUs and software and the processor functions as the plurality of processing units. Second, a processor which is typified by a system-on-chip (SoC) and in which the overall function of a system including a plurality of processing units is implemented by one IC chip is used. As such, the hardware structure of various processing units is formed by one or more of the various processors.

In addition, specifically, the hardware structure of the various processors is an electric circuit (circuitry) which is a combination of circuit elements such as semiconductor elements.

A radiography system described in the following Supplementary Note 1 can be understood from the above description.

Supplementary Note 1

There is provided a radiography system including:
a camera image acquisition processor that, in a case in which radiography is performed using an electronic cassette that detects a radiographic image based on radiation which has been emitted from a radiation source and transmitted through a subject, acquires a camera image obtained by capturing an image of the subject located in an irradiation field which is a region irradiated with the radiation using a camera; a detection processor that detects an in-image cassette position which is a position of the electronic cassette in the camera image, using the camera image; a composite image generation processor that combines the camera image and a positioning index image indicating a set position of the subject, which has been set in advance with respect to the in-image cassette position, to generate a composite image and, in a case in which the in-image cassette position in the camera image is changed with movement of the electronic cassette, changes a display position of the positioning index image in the composite image with the change in the in-image cassette position; and a display control processor that performs control such that the composite image is displayed on a display unit.

An electronic cassette positioning assistance device described in the following Supplementary Note 2, a method for operating an electronic cassette positioning assistance device described in the following Supplementary Note 3, a program for operating an electronic cassette positioning assistance device described in the following Supplementary Note 4 can be understood from the description of each of the above-mentioned embodiments. In each of the above-mentioned embodiments, the console 16 corresponds to the electronic cassette positioning assistance device.

Supplementary Note 2

There is provided an electronic cassette positioning assistance device that, in a case in which radiography is performed using an electronic cassette that detects a radiographic image based on radiation which has been emitted from a radiation source and transmitted through a subject, assists relative positioning between the subject and the electronic cassette. The electronic cassette positioning assistance device includes: a camera image acquisition unit that acquires a camera image obtained by capturing an image of the subject located in an irradiation field which is a region irradiated with the radiation using a camera; a detection unit that detects an in-image cassette position which is a position of the electronic cassette in the camera image, using the camera image; a composite image generation unit that combines the camera image and a positioning index image indicating a set position of the subject, which has been set in advance with respect to the in-image cassette position, to generate a composite image and, in a case in which the in-image cassette position in the camera image is changed with movement of the electronic cassette, changes a display position of the positioning index image in the composite image with the change in the in-image cassette position; and a display controller that performs control such that the composite image is displayed on a display unit.

Supplementary Note 3

There is provided a method for operating an electronic cassette positioning assistance device that, in a case in which radiography is performed using an electronic cassette that detects a radiographic image based on radiation which has been emitted from a radiation source and transmitted through a subject, assists relative positioning between the subject and the electronic cassette. The method includes: a camera image acquisition step of acquiring a camera image obtained by capturing an image of the subject located in an irradiation field which is a region irradiated with the radiation using a camera; a detection step of detecting an in-image cassette position which is a position of the electronic cassette in the camera image, using the camera image; a composite image generation step of combining the camera image and a positioning index image indicating a set position of the subject, which has been set in advance with respect to the in-image cassette position, to generate a composite image and, in a case in which the in-image cassette position in the camera image is changed with movement of the electronic cassette, changing a display position of the positioning index image in the composite image with the change in the in-image cassette position; and a display control step of performing control such that the composite image is displayed on a display unit.

Supplementary Note 4

There is provided a program for operating an electronic cassette positioning assistance device that, in a case in which radiography is performed using an electronic cassette that detects a radiographic image based on radiation which has been emitted from a radiation source and transmitted through a subject, assists relative positioning between the subject and the electronic cassette. The program causes a computer to execute: a camera image acquisition function of acquiring a camera image obtained by capturing an image of the subject located in an irradiation field which is a region irradiated with the radiation using a camera; a detection function of detecting an in-image cassette position which is a position of the electronic cassette in the camera image, using the camera image; a composite image generation function of combining the camera image and a positioning index image indicating a set position of the subject, which has been set in advance with respect to the in-image cassette position, to generate a composite image and, in a case in which the in-image cassette position in the camera image is changed with movement of the electronic cassette, changing a display position of the positioning index image in the composite image with the change in the in-image cassette position; and a display control function of performing control such that the composite image is displayed on a display unit.

The camera 23 may be attached to a portion other than the X-ray source 13, such as the wall or ceiling of the imaging room, as long as it can capture the image of the subject H located in the irradiation field.

In each of the above-described embodiments, the case in which free imaging is performed using the X-ray imaging system 10 installed in the imaging room has been described as an example. However, the invention can also be applied to a case in which free imaging is performed in a hospital room equipped with a bed for the subject H, using a treatment cart which is a portable X-ray generation apparatus.

The invention is not limited to the X-rays and can also be applied to a case in which other types of radiation including γ-rays are used.

The invention is not limited to each of the above-described embodiments and can adopt various configurations without departing from the scope and spirit of the invention. In addition, the invention can be applied to a program and a storage medium storing the program.

EXPLANATION OF REFERENCES

10: X-ray imaging system
11: X-ray generation apparatus
12: X-ray imaging apparatus
13: X-ray source (radiation source)
14: radiation source control device
15: electronic cassette
16: console
20: X-ray tube
21: irradiation field limiter
22: irradiation field display light source
23: camera
25: touch panel
26: voltage generation unit
27: controller
28: irradiation switch
30: display
31: input device
35: imaging order
38: menu-condition table
40, 40-1, 40-2: X-ray image (radiographic image)
41: image file
42: accessory information
50: sensor panel
51: circuit unit
52: housing
52A: front surface
53: transmission plate
55: scintillator
56: optical detection substrate
57A to 57C: marker
60: camera image
65: storage device
66: memory
67: CPU
68: communication unit
69: data bus
75: operation program
76, 105, 128, 130: index image database (DB)
80: camera image acquisition unit
81: detection unit
82: index image acquisition unit 83: composite image generation unit
84: display controller
90, 90G1, 90G2, 90S, 90N, 90O, 106, 106G: positioning index image
91, 107: contour
95: cassette frame (cassette position index)
100: composite image
108A: line of wrinkle
108B: line of bone
115, 121, 125: index image generation unit
120: X-ray image acquisition unit
131: body type specification unit
135: first calculation unit
136: first error processing unit
138: first warning
140: association processing unit
145: imaging range
145-1: divided imaging range (reference imaging range)
145-2: divided imaging range (the other imaging range)
148: bed
150: recommended cassette frame (recommended cassette position index)
155: second calculation unit
156: second error processing unit
158: second warning
160: position detection unit
163: position signal acquisition unit
H: subject
FOV: field of view of camera
RX: imaging region
RA: normal line to front surface of electronic cassette
α: rotation angle about normal line to front surface of electronic cassette
ST100 to ST140: step

What is claimed is:

1. A radiography system comprising:
a camera image acquisition unit that, in a case in which radiography is performed using an electronic cassette that detects a radiographic image based on radiation which has been emitted from a radiation source and transmitted through a subject, acquires a camera image obtained by capturing an image of the subject located in an irradiation field which is a region irradiated with the radiation using a camera;
a detection unit that detects an in-image cassette position which is a position of the electronic cassette in the camera image, using the camera image;
a composite image generation unit that combines the camera image and a positioning index image indicating a set position of the subject, which has been set in advance with respect to the in-image cassette position, to generate a composite image and, in a case in which the in-image cassette position in the camera image is changed with movement of the electronic cassette, changes a display position of the positioning index image in the composite image with the change in the in-image cassette position; and
a display controller that performs control such that the composite image is displayed on a display unit.

2. The radiography system according to claim 1,
wherein the composite image generation unit displays a cassette position index indicating the position of the electronic cassette in the composite image.

3. The radiography system according to claim 1,
wherein, in a case in which the electronic cassette is included in the camera image, the detection unit specifies characteristics of the electronic cassette from the camera image and detects the in-image cassette position.

4. The radiography system according to claim 1,
wherein the positioning index image is a contour image that indicates a contour of a human body model simulating the subject.

5. The radiography system according to claim 1,
wherein the positioning index image is a three-dimensional display image in which the human body model simulating the subject is three-dimensionally displayed.

6. The radiography system according to claim 5, further comprising:
an index image generation unit that generates the positioning index image.

7. The radiography system according to claim 6,
wherein the index image generation unit generates the positioning index image on the basis of the camera image.

8. The radiography system according to claim 6,
wherein the index image generation unit generates the positioning index image on the basis of the radiographic image.

9. The radiography system according to claim 6,
wherein the index image generation unit edits a posture and/or a direction of the subject included in a reference three-dimensional display image on the basis of the camera image to generate an edited three-dimensional display image and uses the generated edited three-dimensional display image as the positioning index image.

10. The radiography system according to claim 1, further comprising:
an index image acquisition unit that accesses an index image database in which a plurality of the positioning index images are registered in advance and acquires the positioning index image.

11. The radiography system according to claim 10,
wherein the positioning index image is registered for each imaging menu defining at least one of imaging procedures, which are information related to an imaging part of the subject or a posture and a direction of the imaging part, in the index image database, and
the index image acquisition unit acquires the positioning index image corresponding to the set imaging menu from the index image database.

12. The radiography system according to claim 10,
wherein the positioning index image is registered for each subject in the index image database, and
the index image acquisition unit acquires the positioning index image corresponding to the subject from the index image database.

13. The radiography system according to claim 10,
wherein the positioning index image is registered for each body type of the subject in the index image database,
the radiography system further comprises a body type specification unit that specifies the body type of the subject, and
the index image acquisition unit acquires the positioning index image corresponding to the body type of the subject specified by the body type specification unit from the index image database.

14. The radiography system according to claim 1, further comprising:
a first calculation unit that calculates a first deviation amount which is an amount of deviation between the set position indicated by the positioning index image and an actual position of the subject; and a first error processing unit that performs first error processing in a case in which the first deviation amount is greater than a predetermined first threshold value.

15. The radiography system according to claim 1, further comprising:

an association processing unit that associates related information of the positioning index image as accessory information of the radiographic image with the radiographic image.

16. The radiography system according to claim 1, wherein, in a case in which long-length imaging that captures each of a plurality of divided imaging ranges, into which a long imaging range including a plurality of imaging parts of the subject is divided, and combines a plurality of the radiographic images corresponding to each divided imaging range to generate a long radiographic image is performed, the detection unit detects the in-image cassette position of the electronic cassette located in a reference divided imaging range, and the composite image generation unit displays a recommended cassette position index indicating a recommended position of the electronic cassette in the other divided imaging range with respect to the in-image cassette position of the electronic cassette located in the reference divided imaging range which has been detected by the detection unit.

17. The radiography system according to claim 16, wherein the composite image generation unit displays the positioning index image in the recommended cassette position index.

18. The radiography system according to claim 16, further comprising:

a second calculation unit that calculates a second deviation amount which is an amount of deviation between the recommended position indicated by the recommended cassette position index and an actual position of the electronic cassette; and a second error processing unit that performs second error processing in a case in which the second deviation amount is greater than a predetermined second threshold value.

19. The radiography system according to claim 1, wherein the camera is attached to the radiation source.

20. A method for operating a radiography system comprising:

a camera image acquisition step of, in a case in which radiography is performed using an electronic cassette that detects a radiographic image based on radiation which has been emitted from a radiation source and transmitted through a subject, acquiring a camera image obtained by capturing an image of the subject located in an irradiation field which is a region irradiated with the radiation using a camera;

a detection step of detecting an in-image cassette position which is a position of the electronic cassette in the camera image, using the camera image;

a composite image generation step of combining the camera image and a positioning index image indicating a set position of the subject, which has been set in advance with respect to the in-image cassette position, to generate a composite image and, in a case in which the in-image cassette position in the camera image is changed with movement of the electronic cassette, changing a display position of the positioning index image in the composite image with the change in the in-image cassette position; and a display control step of performing control such that the composite image is displayed on a display unit.

* * * * *